US012622714B2

(12) United States Patent
Aklog et al.

(10) Patent No.: US 12,622,714 B2
(45) Date of Patent: May 12, 2026

(54) SYSTEMS AND METHODS FOR REMOVING UNDESIRABLE MATERIAL WITHIN A CIRCULATORY SYSTEM DURING A SURGICAL PROCEDURE

(71) Applicant: AngioDynamics, Inc., Latham, NY (US)

(72) Inventors: Lishan Aklog, Scarsdale, NY (US); Michael J. Glennon, Braintree, MA (US)

(73) Assignee: AngioDynamics, Inc., Latham, NY (US)

( * ) Notice: Subject to any disclaimer, the term of this patent is extended or adjusted under 35 U.S.C. 154(b) by 0 days.

(21) Appl. No.: 19/353,713

(22) Filed: Oct. 9, 2025

(65) Prior Publication Data

US 2026/0033846 A1     Feb. 5, 2026

Related U.S. Application Data

(63) Continuation of application No. 19/303,491, filed on Aug. 19, 2025, which is a continuation of application
(Continued)

(51) Int. Cl.
A61B 17/22 (2006.01)
A61B 17/3207 (2006.01)
(Continued)

(52) U.S. Cl.
CPC .......... A61B 17/22 (2013.01); A61B 17/3207 (2013.01); A61M 1/3621 (2013.01);
(Continued)

(58) Field of Classification Search
CPC .............. A61B 17/22; A61B 17/22032; A61B 2017/22079; A61B 17/3207;
(Continued)

(56) References Cited

U.S. PATENT DOCUMENTS 3,701,433 A    10/1972  Krakauer
3,765,536 A    10/1973  Rosenberg
(Continued)

FOREIGN PATENT DOCUMENTS

AU      2019321256 A1    3/2021
CA        3114285 A1    2/2020
(Continued)

*Primary Examiner* — Wesley G Harris
(74) *Attorney, Agent, or Firm* — Kevin Radigan, Esq.; Heslin Rothenberg Farley & Mesiti P.C.

(57) ABSTRACT

A method for capturing dislodged vegetative growth during a surgical procedure is provided. The method includes maneuvering, into a circulatory system, a first cannula having a distal end and an opposing proximal end, such that the first cannula is positioned to capture the vegetative growth en bloc. A second cannula is positioned in fluid communication with the first cannula, such that a distal end of the second cannula is situated in spaced relation to the distal end of the first cannula. A suction force is provided through the distal end of the first cannula so as to capture the vegetative growth. Fluid removed by the suction force is reinfused through the distal end of the second cannula. Subsequent to becoming dislodged, the vegetative growth is captured by the first cannula. A method for capturing a vegetative growth during removal of a pacemaker lead is also provided.

30 Claims, 11 Drawing Sheets

Related U.S. Application Data

No. 19/013,019, filed on Jan. 8, 2025, which is a continuation of application No. 18/985,608, filed on Dec. 18, 2024, which is a continuation of application No. 18/942,929, filed on Nov. 11, 2024, which is a continuation of application No. 18/156,211, filed on Jan. 18, 2023, now Pat. No. 12,446,904, which is a continuation of application No. 16/458,529, filed on Jul. 1, 2019, now Pat. No. 11,589,880, which is a continuation of application No. 15/194,990, filed on Jun. 28, 2016, now Pat. No. 10,383,983, which is a continuation of application No. 14/250,486, filed on Apr. 11, 2014, now Pat. No. 9,402,938, which is a continuation of application No. 13/084,675, filed on Apr. 12, 2011, now Pat. No. 8,734,374, which is a continuation-in-part of application No. 12/187,121, filed on Aug. 6, 2008, now Pat. No. 8,075,510.

(60) Provisional application No. 61/015,301, filed on Dec. 20, 2007.

(51) Int. Cl.
*A61M 1/00* (2006.01)
*A61M 1/36* (2006.01)

(52) U.S. Cl.
CPC .............. *A61M 1/741* (2021.05); *A61M 1/87* (2021.05); *A61B 17/22032* (2013.01); *A61B 2017/22079* (2013.01); *A61B 2017/22094* (2013.01); *A61B 2217/005* (2013.01); *A61M 1/77* (2021.05); *A61M 1/79* (2021.05); *A61M 1/80* (2021.05); *A61M 2202/0014* (2013.01); *A61M 2205/7545* (2013.01)

(58) Field of Classification Search
CPC .... A61B 2017/22094; A61B 2217/005; A61B 2017/2215; A61B 2017/22034; A61M 1/77; A61M 1/3621; A61M 2205/7545; A61M 1/79; A61M 1/84; A61M 2210/12; A61M 2202/0014; A61M 25/10; A61M 1/60; A61M 1/741; A61M 1/76; A61M 1/87; A61M 1/80; A61M 2202/09; A61M 2202/20
See application file for complete search history.

(56) References Cited

U.S. PATENT DOCUMENTS

| | | | |
|---|---|---|---|
| 4,033,345 A | | 7/1977 | Sorenson |
| 4,038,194 A | | 7/1977 | Luceyk |
| 4,056,476 A | | 11/1977 | Mouwen |
| 4,087,363 A | | 5/1978 | Rosemeyer |
| 4,411,783 A | | 10/1983 | Dickens |
| 4,690,762 A | | 9/1987 | Katsura |
| 4,834,743 A | | 5/1989 | Valerio |
| 4,886,487 A | | 12/1989 | Solem |
| 4,892,529 A | | 1/1990 | Valerio |
| 4,919,802 A | | 4/1990 | Katsura |
| 4,954,251 A | | 9/1990 | Barnes |
| 5,011,488 A | * | 4/1991 | Ginsburg ......... A61B 17/22032 604/908 |
| 5,055,198 A | | 10/1991 | Shettigar |
| 5,100,376 A | | 3/1992 | Blake, III |
| 5,133,703 A | | 7/1992 | Boehringer |
| 5,201,703 A | | 4/1993 | Gentelia |
| 5,234,403 A | | 8/1993 | Yoda |
| 5,312,479 A | | 5/1994 | Weinstein |
| 5,372,945 A | * | 12/1994 | Alchas ................... C12M 45/09 435/308.1 |
| 5,380,314 A | | 1/1995 | Herweck |
| 5,407,424 A | | 4/1995 | Lafontaine |
| 5,588,958 A | | 12/1996 | Cunningham |
| 5,603,700 A | | 2/1997 | Daneshvar |
| 5,618,425 A | | 4/1997 | Mitamura |
| 5,695,489 A | | 12/1997 | Japuntich |
| 5,722,964 A | | 3/1998 | Herweck |
| 5,785,700 A | | 7/1998 | Olson |
| 5,788,661 A | | 8/1998 | Japuntich |
| 5,800,457 A | * | 9/1998 | Gelbfish ............... A61F 2/0105 606/200 |
| 6,059,745 A | * | 5/2000 | Gelbfish ................. A61M 1/81 604/9 |
| 6,200,276 B1 | | 3/2001 | Biesel |
| 6,274,055 B1 | | 8/2001 | Zuk, Jr. |
| 6,451,257 B1 | | 9/2002 | Flamer |
| 6,558,341 B1 | | 5/2003 | Swisher |
| 6,682,656 B2 | | 1/2004 | Rothman |
| 6,719,717 B1 | | 4/2004 | Johnson |
| 6,767,353 B1 | | 7/2004 | Shiber |
| 6,773,670 B2 | | 8/2004 | Stringer |
| 6,936,060 B2 | | 8/2005 | Hogendijk |
| 7,217,361 B2 | | 5/2007 | Connor |
| 7,279,107 B2 | | 10/2007 | Hoegberg |
| 7,353,956 B2 | | 4/2008 | Lynn |
| 7,429,325 B2 | | 9/2008 | Ingvarsson |
| 7,497,944 B2 | | 3/2009 | Hoegberg |
| 7,621,407 B2 | | 11/2009 | Herbst |
| 7,713,227 B2 | | 5/2010 | Wholey |
| 7,794,420 B2 | | 9/2010 | Perovitch |
| 7,927,400 B2 | | 4/2011 | Graber |
| 7,938,820 B2 | | 5/2011 | Webster |
| 8,080,086 B2 | | 12/2011 | Graber |
| 8,187,465 B2 | | 5/2012 | Nierich |
| 8,535,283 B2 | | 9/2013 | Heaton |
| 8,586,324 B2 | | 11/2013 | Leach |
| D724,179 S | | 3/2015 | Keenan |
| 8,992,403 B2 | | 3/2015 | Eberle |
| 9,555,353 B2 | | 1/2017 | Graber |
| 9,675,914 B2 | | 6/2017 | Rivera |
| 9,815,038 B2 | | 11/2017 | Leach |
| 9,827,364 B2 | | 11/2017 | Peticca |
| 9,907,899 B2 | | 3/2018 | Kim |
| 9,937,448 B2 | | 4/2018 | Yost |
| 10,111,999 B2 | | 10/2018 | Muennich |
| 10,197,026 B2 | | 2/2019 | Salsbury |
| 10,213,582 B2 | | 2/2019 | Garrison |
| 10,226,263 B2 | | 3/2019 | Look |
| 10,226,598 B2 | | 3/2019 | Chou |
| 10,390,849 B2 | | 8/2019 | Kugler |
| 10,456,555 B2 | | 10/2019 | Garrison |
| 10,500,330 B2 | | 12/2019 | Schwarz |
| 10,682,454 B2 | | 6/2020 | Coulthard |
| 10,967,111 B2 | | 4/2021 | Iida |
| 11,065,018 B2 | | 7/2021 | Buck |
| 11,154,314 B2 | | 10/2021 | Quick |
| 11,253,277 B2 | | 2/2022 | Buck |
| 11,259,821 B2 | | 3/2022 | Buck |
| 11,266,825 B2 | | 3/2022 | Peter |
| 11,439,799 B2 | | 9/2022 | Buck |
| 11,457,936 B2 | | 10/2022 | Buck |
| 11,553,935 B2 | | 1/2023 | Buck |
| 11,554,005 B2 | | 1/2023 | Merritt |
| 11,559,382 B2 | | 1/2023 | Merritt |
| 11,589,880 B2 | | 2/2023 | Aklog |
| 11,607,478 B2 | | 3/2023 | Gadrat |
| 11,633,272 B2 | | 4/2023 | Buck |
| 11,642,209 B2 | | 5/2023 | Merritt |
| 11,883,570 B2 | | 1/2024 | Yao |
| 12,171,917 B1 | | 12/2024 | Buck |
| 12,245,781 B2 | | 3/2025 | Aklog |
| 12,446,904 B2 | | 10/2025 | Aklog |
| 2001/0049486 A1 | | 12/2001 | Evans |
| 2002/0138094 A1 | | 9/2002 | Borillo |
| 2003/0144687 A1 | | 7/2003 | Brady |
| 2004/0019310 A1 | | 1/2004 | Hogendijk |
| 2004/0102697 A1 | | 5/2004 | Evron |
| 2004/0102728 A1 | | 5/2004 | Foster |
| 2004/0153118 A1 | | 8/2004 | Clubb |
| 2005/0004534 A1 | | 1/2005 | Lockwood |
| 2005/0189283 A1 | | 9/2005 | Smit |

(56) References Cited

U.S. PATENT DOCUMENTS

| | | | |
|---|---|---|---|
| 2006/0041228 A1* | 2/2006 | Vo | A61B 17/12045 |
| | | | 604/101.04 |
| 2006/0047301 A1 | 3/2006 | Ogle | |
| 2006/0270974 A1 | 11/2006 | Goff | |
| 2008/0314834 A1 | 12/2008 | Herbst | |
| 2011/0009837 A1 | 1/2011 | Schreiner | |
| 2014/0364833 A1 | 12/2014 | Christensen | |
| 2015/0173782 A1 | 6/2015 | Garrison | |
| 2015/0314057 A1 | 11/2015 | Labib | |
| 2015/0352325 A1 | 12/2015 | Quick | |
| 2016/0106353 A1 | 4/2016 | Schuetz | |
| 2018/0042623 A1 | 2/2018 | Batiste | |
| 2018/0338770 A1 | 11/2018 | Mogi | |
| 2019/0015398 A1 | 1/2019 | Osborne | |
| 2019/0184076 A1 | 6/2019 | Gourlay | |
| 2020/0030504 A1 | 1/2020 | Igarashi | |
| 2020/0046368 A1 | 2/2020 | Merritt | |
| 2020/0164117 A1 | 5/2020 | Culhane | |
| 2021/0093758 A1 | 4/2021 | Corrales | |
| 2021/0186537 A1 | 6/2021 | Buck | |
| 2021/0186812 A1 | 6/2021 | Pennie | |
| 2021/0187244 A1 | 6/2021 | Buck | |
| 2021/0315598 A1 | 10/2021 | Buck | |
| 2021/0316127 A1 | 10/2021 | Buck | |
| 2021/0402086 A1 | 12/2021 | Jokaji | |
| 2022/0184290 A1 | 6/2022 | Herzlinger | |
| 2022/0226555 A1 | 7/2022 | Sunenshine | |
| 2022/0240959 A1 | 8/2022 | Quick | |
| 2022/0346813 A1 | 11/2022 | Quick | |
| 2022/0346814 A1 | 11/2022 | Quick | |
| 2022/0387759 A1 | 12/2022 | Turovskiy | |
| 2023/0015259 A1 | 1/2023 | Buck | |
| 2023/0062809 A1 | 3/2023 | Merritt | |
| 2023/0233311 A1 | 7/2023 | Merritt | |

FOREIGN PATENT DOCUMENTS

| | | |
|---|---|---|
| CN | 112867455 A | 5/2021 |
| EP | 0122748 A1 | 10/1984 |
| EP | 0518975 B1 | 5/1997 |
| EP | 3836855 A4 | 8/2022 |
| EP | 3362116 B1 | 6/2023 |
| JP | 1983112549 A | 7/1983 |
| JP | 2021534851 A | 12/2021 |
| WO | 1997009106 A1 | 3/1997 |
| WO | 2006029270 A1 | 3/2006 |
| WO | 2006100651 A1 | 9/2006 |
| WO | 2014093845 A1 | 6/2014 |
| WO | 2015071852 A2 | 5/2015 |
| WO | 2016067246 A1 | 5/2016 |

* cited by examiner

SYSTEMS AND METHODS FOR REMOVING UNDESIRABLE MATERIAL WITHIN A CIRCULATORY SYSTEM DURING A SURGICAL PROCEDURE

CROSS REFERENCE TO RELATED APPLICATIONS

This application is a continuation of U.S. application Ser. No. 19/303,491 filed on Aug. 19, 2025, which is a continuation of U.S. application Ser. No. 19/013,019 filed on Jan. 8, 2025, which is a continuation of U.S. application Ser. No. 18/985,608 filed on Dec. 18, 2024, which is a continuation of U.S. application Ser. No. 18/942,929 filed on Nov. 11, 2024, which is a continuation of U.S. application Ser. No. 18/156,211 filed on Jan. 18, 2023, which is a continuation of U.S. patent application Ser. No. 16/458,529, filed Jul. 1, 2019 (now U.S. Pat. No. 11,589,880), which is a continuation of U.S. patent application Ser. No. 15/194,990, filed Jun. 28, 2016 (now U.S. Pat. No. 10,383,983), which is a continuation of U.S. patent application Ser. No. 14/250,486, filed Apr. 11, 2014 (now U.S. Pat. No. 9,402,938), which is a continuation of U.S. patent application Ser. No. 13/084,675, filed Apr. 12, 2011 (now U.S. Pat. No. 8,734,374), which is a continuation-in-part of U.S. patent application Ser. No. 12/187,121, filed Aug. 6, 2008 (now U.S. Pat. No. 8,075,510), which claims the benefit of U.S. Provisional Application No. 61/015,301, filed Dec. 20, 2007, all of which are hereby incorporated herein by reference in their entirety.

TECHNICAL FIELD

The present invention relates to systems and methods for removing undesirable materials from a site of interest within the circulatory system. More particularly, the present invention relates to systems and methods for removing substantially en bloc clots, thrombi, and emboli, among others, from within heart chambers, as well as medium to large vessels, while reinfusing fluid removed from the site of interest back into the patient to minimize fluid loss.

Background Art

Many of the most common and deadly diseases afflicting mankind result from or in the presence of undesirable material, most notably blood clots, in the blood vessels and heart chambers. Examples of such diseases include myocardial infarction, stroke, pulmonary embolism, deep vein thrombosis, atrial fibrillation, infective endocarditis, etc. The treatment of some of these conditions, which involve smaller blood vessels, such as myocardial infarction and stroke, has been dramatically improved in recent years by targeted mechanical efforts to remove blood clots from the circulatory system. Other deadly conditions, which involve medium to large blood vessels or heart chambers, such as pulmonary embolism (½ million deaths per year) or deep venous thrombosis (2-3 million cases per year) have not benefited significantly from such an approach. Present treatment for such conditions with drugs or other interventions is not sufficiently effective. As a result, additional measures are needed to help save lives of patients suffering from these conditions.

The circulatory system can be disrupted by the presence of undesirable material, most commonly blood clots, but also tumor, infective vegetations, and foreign bodies, etc. Blood clots can arise spontaneously within the blood vessel or heart chamber (thrombosis) or be carried through the circulation from a remote site and lodge in a blood vessel (thromboemboli).

In the systemic circulation, this undesirable material can cause harm by obstructing a systemic artery or vein. Obstructing a systemic artery interferes with the delivery of oxygen-rich blood to organs and tissues (arterial ischemia) and can ultimately lead to tissue death or infarction. Obstructing a systemic vein interferes with the drainage of oxygen-poor blood and fluid from organs and tissues (venous congestion) resulting in swelling (edema) and can occasionally lead to tissue infarction.

Many of the most common and deadly human diseases are caused by systemic arterial obstruction. The most common form of heart disease, such as myocardial infarction, results from thrombosis of a coronary artery following disruption of a cholesterol plaque. The most common causes of stroke include obstruction of a cerebral artery either from local thrombosis or thromboemboli, typically from the heart. Obstruction of the arteries to abdominal organs by thrombosis or thromboemboli can result in catastrophic organ injury, most commonly infarction of the small and large intestine. Obstruction of the arteries to the extremities by thrombosis or thromboemboli can result in gangrene.

In the systemic venous circulation, undesirable material can also cause serious harm. Blood clots can develop in the large veins of the legs and pelvis, a common condition known as deep venous thrombosis (DVT). DVT arises most commonly when there is a propensity for stagnated blood (long-haul air travel, immobility) and clotting (cancer, recent surgery, especially orthopedic surgery). DVT causes harm by (1) obstructing drainage of venous blood from the legs leading to swelling, ulcers, pain and infection and (2) serving as a reservoir for blood clot to travel to other parts of the body including the heart, lungs (pulmonary embolism) and across a opening between the chambers of the heart (patent foramen ovale) to the brain (stroke), abdominal organs or extremities.

In the pulmonary circulation, the undesirable material can cause harm by obstructing pulmonary arteries, a condition known as pulmonary embolism. If the obstruction is upstream, in the main or large branch pulmonary arteries, it can severely compromise total blood flow within the lungs and therefore the entire body, resulting in low blood pressure and shock. If the obstruction is downstream, in large to medium pulmonary artery branches, it can prevent a significant portion of the lung from participating in the exchange of gases to the blood resulting low blood oxygen and build up of blood carbon dioxide. If the obstruction is further downstream, it can cut off the blood flow to a smaller portion of the lung, resulting in death of lung tissue or pulmonary infarction.

The presence of the undesirable material within the heart chambers can cause harm by obstructing flow or by serving as a reservoir for emboli to other organs in the body. The most common site for obstruction within the heart is in the heart valves. Infective vegetations, a condition known as endocarditis, can cause partial obstruction to flow across a valve before destroying the valve. Patients with prosthetic valves, especially mechanical valves, are particularly prone to valve thrombosis and obstruction. The heart chambers are the most common source of emboli (cardioemboli) to the systemic circulation, including stroke. Emboli tend to arise from areas that are prone to stagnation of blood flow under pathologic conditions. The left atrial appendage in patients with atrial fibrillation is prone to thrombosis, as well as the left ventricular apex in patients with acute myocardial infarction or dilated cardiomyopathy. Infected vegetations or thrombi on the heart valves are also common sources of emboli. Undesirable material such as blood clots and infected vegetations can reside in the chambers of the right heart (atrium and ventricle), often associated with prosthetic material such as pacemaker leads or long-term indwelling catheters.

The most effective treatment for conditions resulting from the presence of blood clots or other undesirable materials within the circulation is, of course, to stabilize or eliminate the material before it has embolized. Alternatively, if obstruction to flow has already occurred but before the obstruction has caused permanent harm (infarction, shock, death), the material can be eliminated by utilizing biologic or mechanical means.

Biologic treatments involve the delively of agents to the material, which either dissolve the material or, at a minimum, stabilize it until the body can eliminate it. In the case of infective vegetations, antimicrobial agents can, over time, decrease the chances of embolization. In the case of blood clots, the agents include 1) anticoagulant agents (heparin, warfarin, etc.) which prevent propagation of blood clots; and 2) more potent thrombolytic agents (streptokinase, urokinase, tPA, etc.) which actively dissolve clots. The agents are usually delivered systemically, i.e., into a peripheral or central vein and allowed to circulate throughout the body. Thrombolytic agents can also be delivered through a catheter directly to the blood clot which can increase its effectiveness by increasing local concentrations but this does not completely eliminate the absorption into systemic circulation throughout the body.

Thrombolytic agents have been shown to increase survival in patients with hemodynamically significant pulmonary embolism as documented by echocardiographic evidence of right ventricular strain. The use of thrombolytic agents is the standard of care in this subgroup of patients with a high 20-25% early mortality. They are commonly used to dissolve clots in other blood vessels including arteries to heart, abdominal organs and extremities.

There are two primary disadvantages to thrombolytic agents. First, every cell in the body is exposed to the agent which can lead to serious and often life threatening bleeding complications in remote areas such as the brain and stomach. The risk of major bleeding complications can be as high as 25% and the risk of often fatal bleeding into the brain can go up to 3%. Second, blood clots undergo a process called organization where the soft gel-like red/purple clot is transformed into a firmer, whitish clot by the cross-linking of proteins such as fibrin. Organized clots are much less amenable to treatment with thrombolytic agents. Thromboemboli, such as pulmonary emboli, can contain a significant amount of organized clot since the thrombus frequently developed at its original site (e.g., the deep veins of the legs) over a long period of time prior to embolizing to the remote site (e.g., the lungs).

Mechanical treatments involve the direct manipulation of the material to eliminate the obstruction. This can involve aspiration, maceration, and compression against the vessel wall, or other types of manipulation. The distinct advantage of mechanical treatment is that it directly attacks the offending material and eliminates the vascular obstruction independent of the specific content of the offending material. Mechanical treatments, if feasible, can usually prove to be superior to biologic treatments for vascular obstruction. Procedural success rates tend to be higher. The best example of this advantage is in the treatment of acute myocardial infarction. Although thrombolytic therapy has had a major impact on the management of patient with myocardial infarction, this option is now relegated to a distant second choice. The clear standard of care today for an acute myocardial infarction is an emergency percutaneous coronary intervention during which the coronary artery obstruction is relieved by aspiration, maceration or balloon compression of the offending thrombus. This mechanical approach has been shown to decrease the amount of damaged heart tissue and improve survival relative to the thrombolytic biological approach.

Mechanical treatment, however, has played a limited role in the removal of blood clots found in larger blood vessels such as pulmonary arteries and heart chambers. Surgical pulmonary embolectomy involves opening the pulmonary artery and removing the offending clot under direct vision. This operation has been performed for nearly 100 years, but did not become practical until the introduction of the heart lung machine. Even then, it was generally relegated to a salvage procedure in moribund patients in whom all other options had been exhausted because of the inherent danger in the surgery and the recovery period. While surgical pulmonary embolectomy is very effective in completely evacuating pulmonary emboli whether soft-fresh and firm-organized clot, it is an invasive procedure.

Recent data has shown that the early outcomes with surgical pulmonary embolectomy are excellent, at least as good as thrombolytic treatment, as long as the procedure is performed in a timely fashion before the patient becomes very ill or suffers a cardiac arrest. The long term outcomes of patients surviving surgical pulmonary embolectomy have always been very good. Although these data have generated a renewed interest in performing surgical pulmonary embolectomy, its use remains limited because of the invasiveness of the procedure. Although minimally invasive approaches have been described, the standard procedure requires a 20-25 cm incision through the sternal bone and placing the patient on cardiopulmonary bypass (the heart-lung machine).

Catheter-based removal of blood clots from larger blood vessels (e.g., pulmonary arteries) and heart chambers has had limited success, at least compared to smaller blood vessels (e.g., coronary arteries). Catheter pulmonary embolectomy, where the pulmonary emboli are removed percutaneously using one of several techniques, has been around for nearly 30 years but few patients currently receive these therapies. These techniques can be subdivided into three categories. With fragmentation thrombectomy, the clot is broken into smaller pieces, most of which migrate further downstream, decreasing the central obstruction but resulting in a "no-reflow" phenomenon, It is sometimes used in combination with thrombolytics which preclude their use as an alternative to thrombolytics. With the rheolytic thrombectomy, high velocity saline jets create a Venturi effect and draw the fragments of the clot into the catheter. Finally the aspiration techniques draw the clot into a catheter via suction. With a Greenfield embolectomy, the catheter with the attached clot is repeatedly drawn out of the vein. All of these techniques rely on catheters which are small compared to the size of the clots and blood vessels. Their limited success is likely related to their inability to achieve a complete en-bloc removal of the material without fragmentation.

The experience with catheter-based treatment of deep venous thrombus has also had limited success. The operator must use relatively small catheters to remove or break up large amounts of well embedded clot. This procedure is therefore time-consuming, inefficient and ultimately not very effective in removal of the whole clot.

It is clear that all of the therapeutic options available to patients with clot or other undesirable material in medium or large blood vessels, such as those with pulmonary embolism, have serious limitations. Anticoagulation only limits propagation of clot, it does not remove it. Thrombolytic therapy is not targeted, carries a real risk of major bleeding, and is not very effective in firm/organized clots. Catheter embolectomy uses technology developed for small blood vessels, does not scale well to material residing in medium and large vessels or heart chambers, and thus is not very effective. Surgical embolectomy is highly effective but highly invasive. There is a real need for a direct mechanical treatment that is as effective as surgical embolectomy but can be performed using endovascular techniques.

Current efforts to apply existing catheter embolectomy technologies to medium to large blood vessels and heart chambers encounter at least two obstacles: fragmentation and excessive blood loss. Techniques which depend on fragmentation of the material tend to be inefficient and ineffective in medium to large blood vessels and heart chambers because the flow of blood will carry a significant portion of the fragmented material away before it can be captured in the catheter. On the other hand, techniques which depend on aspiration of undesirable material will result in excessive blood loss as the size of the catheter increases.

A need therefore exists for a system and method to endovascularly remove undesirable material residing in medium to large blood vessels and heart chambers with minimal fragmentation and without excessive blood loss.

SUMMARY OF THE INVENTION

The present invention relates generally to systems and methods for removing undesirable material residing in vessels, such as blood vessels, or within chambers of the heart. More specifically, the subject invention relates to systems and methods for using a cannula to remove substantially en bloc, from a site of obstruction or interest, an undesirable material, such as blood clots, embolisms and thromboembolisms, without significant fragmentation and without excessive fluid loss. In addition, the systems and methods of the present invention may simultaneously reinfuse aspirated (i.e., removed) and filtered fluid, such as blood, back into the patient on a substantially continuous basis to minimize any occurrences of fluid loss and/or shock. The subject invention may be particularly useful, but may not be limited to, the removal of blood clots, tumors, infective vegetations and foreign bodies from medium to large blood vessels and heart chambers.

In one embodiment, a system for removing an undesirable material from within a vessel is provided. The system includes a first cannula having a distal end and an opposing proximal end. The distal end of the first cannula, in an embodiment, may include or may be deployable to a diameter relatively larger than that of the proximal end. The first cannula may be designed for maneuvering within the vessel to a site of interest, such that an undesirable material can be captured substantially en bloc through the distal end and removed along the first cannula away from the site. The system may also include a pump, in fluid communication with the proximal end of the first cannula, so as to provide a sufficient suction force for removing the undesirable material from the site of interest. The system may further include a second cannula in fluid communication with the pump, so that fluid removed from the site of interest by the first cannula can be directed along the second cannula and reinfused through a distal end of the second cannula. In one embodiment, the distal end of the second cannula may be situated in spaced relation to the distal end of the first cannula. The system may also be provided with a filter device positioned in fluid communication with the first cannula. The filter device, in an embodiment, may act to entrap or capture the undesirable material and remove it from the fluid flow. The system may further be provided with a reservoir in fluid communication with the filter device. The reservoir may act to transiently collect fluid being directed from the filter device and to provide a source of fluid for reinfusion by the second cannula. A second filter may also be included in fluid communication between the pump and the second cannula, so as to remove, prior to reinfusion, any debris that may have escaped from the filter device from the fluid flow.

In another embodiment, there is provided a method for removing an undesirable material from within a vessel. The method includes initially maneuvering a first cannula having a distal end and an opposing proximal end to a site of interest within the vessel, such that the distal end of the first cannula is positioned adjacent to the undesirable material. Next, a second cannula, in fluid communication with the first cannula, may be positioned such that its distal end can be situated in spaced relation to the distal end of the first cannula. Thereafter, a suction force may be provided through the distal end of the first cannula to the site of interest, so as to remove, through the distal end of the first cannula, the undesirable material substantially en bloc from the site of interest. Subsequently, any fluid removed along with the undesirable material may be reinfused, through the distal end of the second cannula, to a location in spaced relation from the distal end of the first cannula. The suction and reinfusion of blood can occur, in an embodiment, continuously for a desired duration to minimize fluid loss in the patient. Alternatively, the step of suctioning an undesirable material can occur at an intermittent pulse for a desired duration following reinfusion of the removed fluid.

In a further embodiment, an apparatus for removing an undesirable material from within a vessel is provided. The apparatus includes an elongated tube having a distal end through which an undesirable material can be captured, a pathway extending along the tube to provide a passage for transporting the undesirable material from the distal end, and a proximal end in opposing relations to the distal end through which the undesirable material can exit. The apparatus also includes a funnel situated at the distal end of the tube, and designed for deployment between an flared open position and a collapsed closed position, so as to better engage and capture the undesirable material. The apparatus further includes a mechanism positioned about a distal portion of the tube, which mechanism, upon actuation, can deploy the funnel between the closed position and the open position. In one embodiment, the funnel includes a plurality of strips, with each strip being pivotally coupled at one end to the distal end of the tube. The funnel may also include a substantially impermeable membrane extending across a space between adjacent strips, such that the membrane, in connection with the strips define the shape of the funnel, The mechanism, in an embodiment, includes a balloon positioned circumferentially about the tube at a location proximal to the funnel, and an attachment mechanism provided with one end attached to the funnel and an opposite end attached to the balloon. By design, upon expansion of the balloon, the attachment mechanism can pull on the funnel to deploy it into a flared open position. The apparatus may also include a jacket positioned circumferentially about the distal end of the tube, and extending from the funnel to the balloon to protect the vessel from potential irritation that may be caused by the balloon and the strips defining the funnel. As the jacket may be attached to the funnel and the balloon, in one embodiment, the jacket may act as the mechanism for deploying the funnel into a flared open position upon expansion of the balloon.

BRIEF DESCRIPTION OF THE DRAWINGS

These and other features and advantages of the present invention will become more apparent from the following detailed descriptions taken in conjunction with the accompanying drawings wherein like reference characters denote corresponding parts throughout the several views.

DETAILED DESCRIPTION OF SPECIFIC EMBODIMENTS

As noted above, existing catheter techniques may not be effective in removing undesirable material, such as clots, from medium and large size blood vessels or from heart chambers, because these catheters tend to be small relative to the material to be removed. As a result, the material often needs to be fragmented in order to fit within the catheter. However, with fragmentation, the chances of the fragments being carried away in the bloodstream increases, resulting in downstream obstruction. If the catheter is enlarged to accommodate the larger structure and material, such a catheter may aspirate an unacceptable volume of blood, resulting in excessive fluid loss and/or shock in the patient.

The present invention overcomes the deficiencies of existing devices and techniques and can act to remove substantially en bloc (i.e., wholly or entirely) undesirable material, such as thrombi and emboli, from the vasculature, including medium to large size blood vessels, and from heart chambers. Vessels from which the undesirable material may be removed, in accordance with an embodiment of the present invention, include, for example, those within the pulmonary circulation (e.g., pulmonary arteries), systemic venous circulation (e.g., vena cavae, pelvic veins, leg veins, neck and arm veins) or alterial circulation (e.g., aorta or its large and medium branches). The heart chambers may be, for example, in the left heart (e.g., the left ventricular apex and left atrial appendage), right heart (e.g., right atrium and right ventricle), or on its valves. The present invention can also act to remove tumors, infective vegetations and other foreign bodies.

Although reference is made to medium and large vessels, it should be appreciated that the systems and methods, hereinafter disclosed, can be scaled and adapted for use within smaller vessels within the body, if desired.

Figure 1:
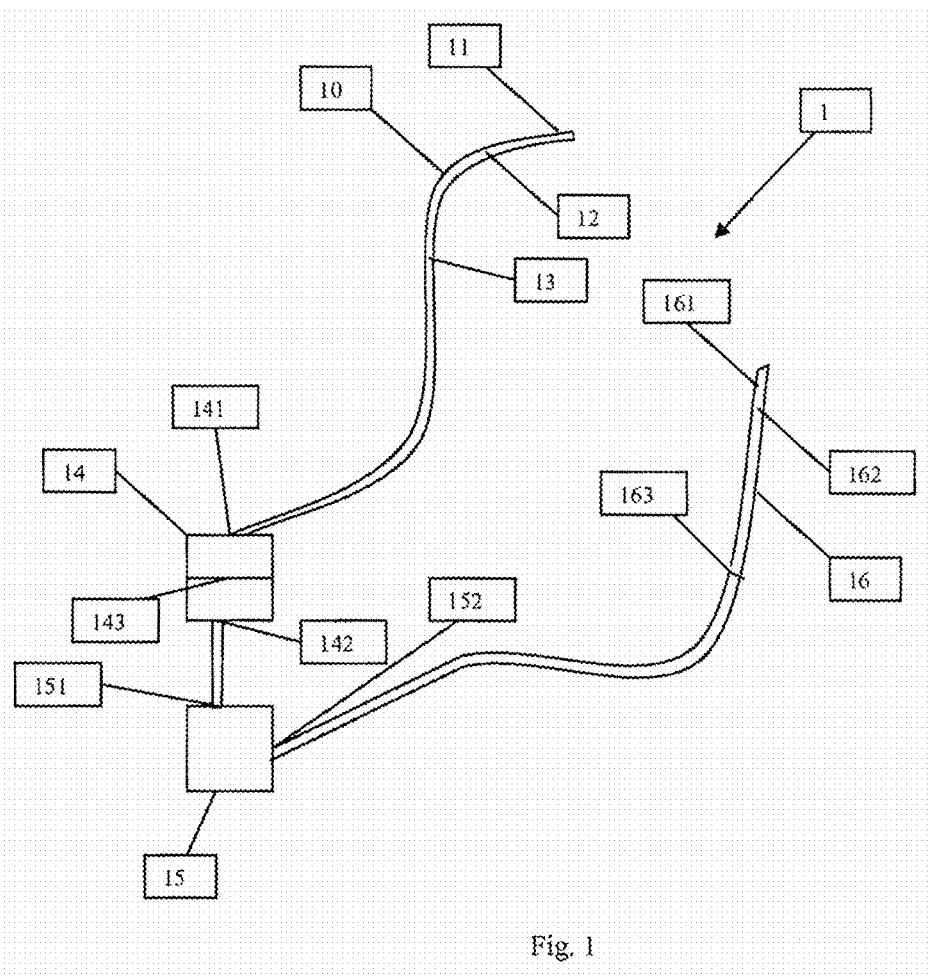
FIG. 1 illustrates system for removing an undesirable material from within a vessel in accordance with one embodiment of the present invention.

Referring now to FIG. 1, there is illustrated a system 1 for removing an undesirable material, substantially en bloc, from an obstruction site or site of interest within the vasculature, and for reinfusion of fluid removed (i.e., suctioned or aspirated) from the site of interest back into a patient, in order to minimize fluid loss within the patient. System 1, in an embodiment, may be provided with a first or suction cannula 10 for capturing and removing en bloc the undesirable material from the site of interest, such as that within a blood vessel or a heart chamber. Cannula 10, in an embodiment, may be an elongated tube and may include a distal end 11 through which the undesirable material can be captured and removed. Cannula 10 may also include a lumen or pathway 12 extending along a body portion of cannula 10. Pathway 12, in one embodiment, provides a passage along which the captured material and aspirated circulatory fluid, such as blood, that may be captured therewith may be transported and directed away from the site of interest. Cannula 10 may further include a proximal end 13 in opposing relations to the distal end 11, and through which the captured material may exit from the cannula 10.

Since cannula 10 may be designed for introduction into the vasculature, for instance, through a peripheral blood vessel, and may need to subsequently be maneuvered therealong to the site of interest, cannula 10, in an embodiment, may be made from a pliable material. In addition, as cannula 10 may be used to introduce a suction force to the site of interest for capturing the undesirable material, cannula 10 may be made from a sufficiently stiff material or may be reinforced with a sufficiently stiff material, so as not to collapse under a suction force. In one embodiment, cannula 10 may be constructed from a biocompatible material, such as polyvinyl chloride, polyethylene, polypropylene, polyurethane, polyether block amide (Pebax®), silicone, or a combination thereof.

In certain instances, it may be desirable to maneuver cannula IO to the site of interest using image guidance, for example, using fluoroscopy or echocardiography. In order to permit cannula 10 to be visualized, cannula 10, in an embodiment, may also include a radioopaque material or any material capable of being visualized.

Figures 2A, 2B, 2C:
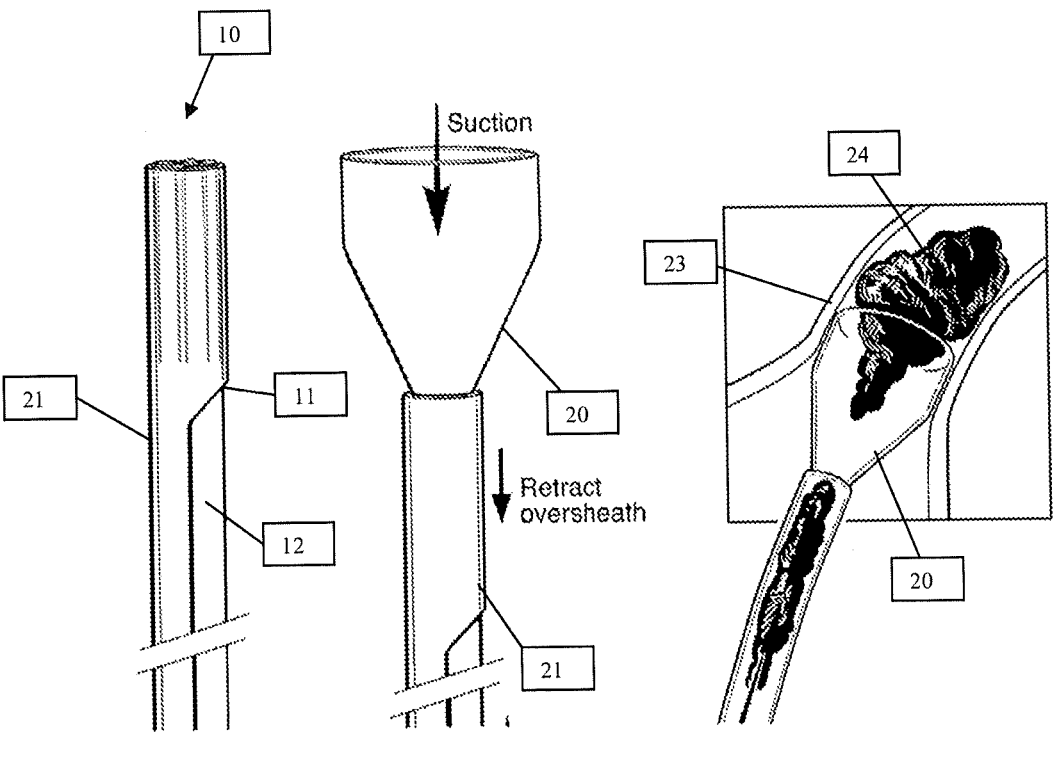
FIGS. 2A-H illustrate a distal end of a suction cannula in operation in connection with the system shown in FIG. 1.
Figure 2D:
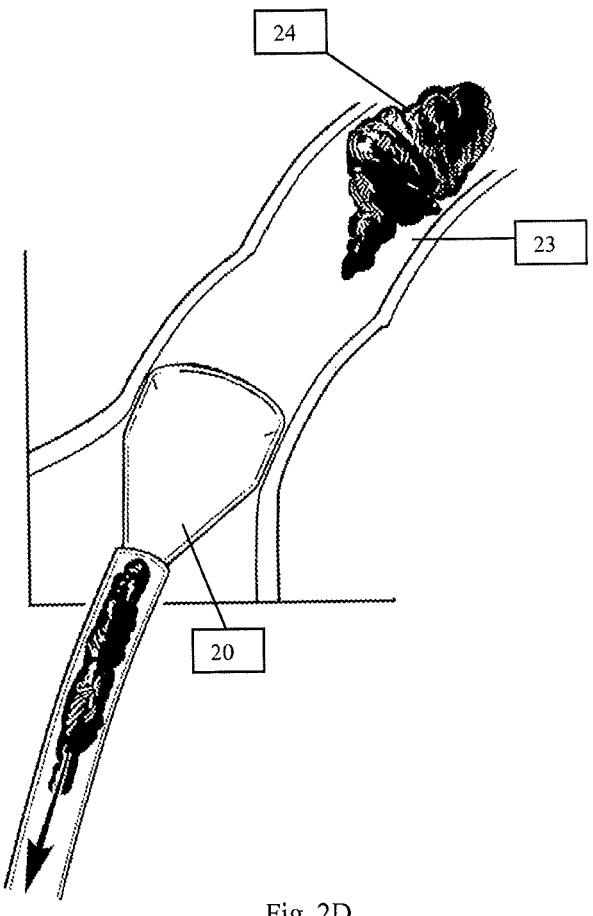

To better engage and capture the undesirable material substantially en bloc and without significant fragmentation, the distal end 11 of cannula 10 may be designed to have a diameter that can be relatively larger than that of the proximal end 13. In one embodiment, as illustrated in FIGS. 2A-D, distal end 11 of cannula 10 may be in the shape of a funnel 20, and may be provided with a diameter, for example, approximately at least three times that of pathway 12. Of course, depending on the surgical procedure being implemented, the ratio between the diameter of funnel 20 and pathway 12 can be varied, if so desired. Funnel 20, with its design, may be placed directly at a site of interest 23 to engage undesirable material 24 (FIG. 2C), or spatially away from the site of interest 23 to capture the undesirable material 24 (FIG. 2D). In a situation where the distal end 11 may be situated spatially away from the site of interest, by providing distal end 11 with funnel 20, a vortex effect may be generated during suctioning to better direct the undesirable material into the funnel 20. It is believed that fluid flowing into funnel 20 can often exhibit a laminar flow circumferentially along the interior surface of the funnel 20 to generate a vortex flow into the distal end 11 of suction cannula 10. Thus, in the presence of a vortex flow, such a flow can act to direct the undesirable material toward the distal end 11 to allow the material to subsequently be pulled into the distal end by suctioning.

To provide a funnel shaped distal end, cannula 10 may include, in an embodiment, a sheath 21 circumferentially situated about distal end 11 of cannula 10. Sheath 21, as illustrated, may be designed to slide toward as well as away from the distal end 11 of cannula 10. In that way, when the distal end 11 is positioned at the site of interest 23, and sheath 21 is retracted (i.e., slid away from the distal end 11), funnel 20 may be exposed and expanded into the desired shape in order to engage undesirable material 24. To collapse funnel 20, sheath 21 may be advanced toward the distal end 11 and over the funnel 20. Thereafter, cannula 10 may be maneuvered from the site of interest 23.

Figures 2E, 2F, 2G:
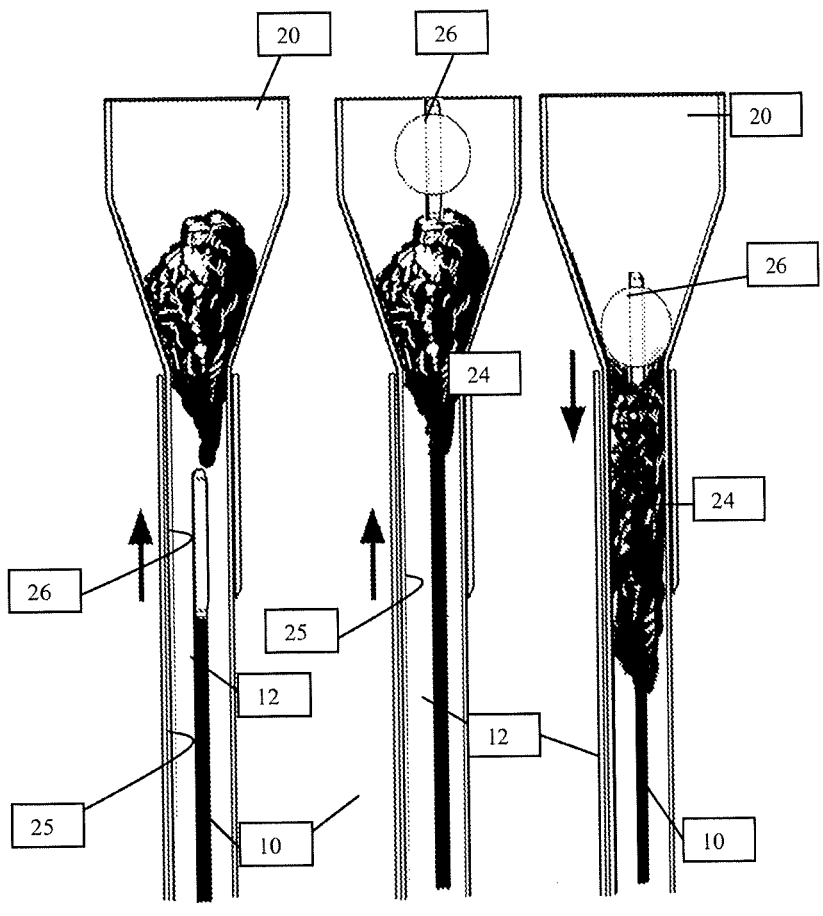
Figure 2H:
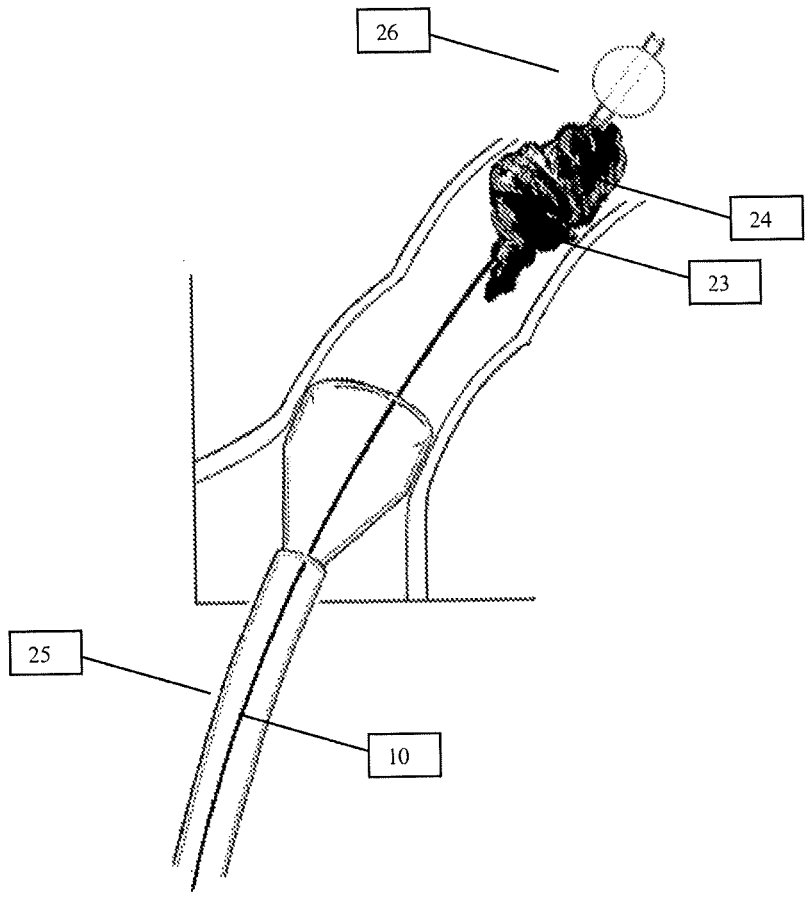

In order to enhance capture and removal of the undesirable material 24, looking now at FIGS. 2E-G, cannula 10 may be designed to allow introduction of a catheter 25 with balloon 26 to the site of interest. In an example where the undesirable material 24 may be entrapped within funnel 20, catheter 25 with balloon 26 may be directed along the lumen or pathway 12 of cannula 10 and into funnel 20. Once catheter 25 has been advanced past the undesirable material 24 within funnel 20, balloon 26 may be inflated to a size sufficient to pull on the undesirable material entrapped within funnel 20. As balloon 26 is pulled down the funnel 20 towards pathway 12, balloon 26 can dislodge the entrapped material and can eventually partially or substantially occlude a pathway 12, distal to the undesirable material 24, which in essence occludes the fluid communication between cannula 10 and the vessel. The suction force within pathway 12, as a result, can be enhanced to better remove the undesirable material. Similarly, as shown in FIG. 2H, in a situation where undesirable material 24 may be firmly lodged in the vessel at the site of interest 23 and the suction applied by cannula 10, spatially situated away from the site of interest 23, may be insufficient to dislodge the undesirable material 24, catheter 25 and balloon 26 may be advanced past the distal end of cannula 10 and past the undesirable material 24 at the site of interest 23. Once past the undesirable material 24 the balloon 26 may be inflated and as balloon is withdrawn back towards the distal end 11 of cannula 10, it can dislodge the undesirable material and allow the suction to draw it into the distal end of cannula 10. Of course, this approach can also be applied when cannula 10 is situated directly at the site of interest 23 and the suction force may be insufficient to dislodge the undesirable material 24.

Figure 3A:
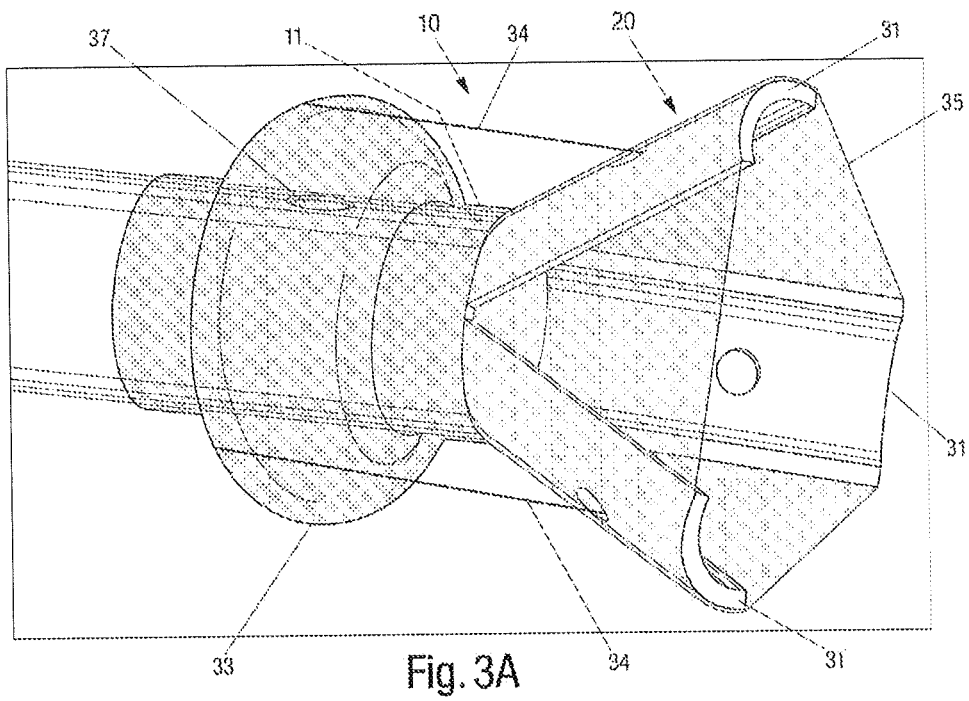
FIGS. 3A-B illustrate an alternate distal end of a suction cannula used in connection with the system shown in FIG. 1.
Figure 3B:
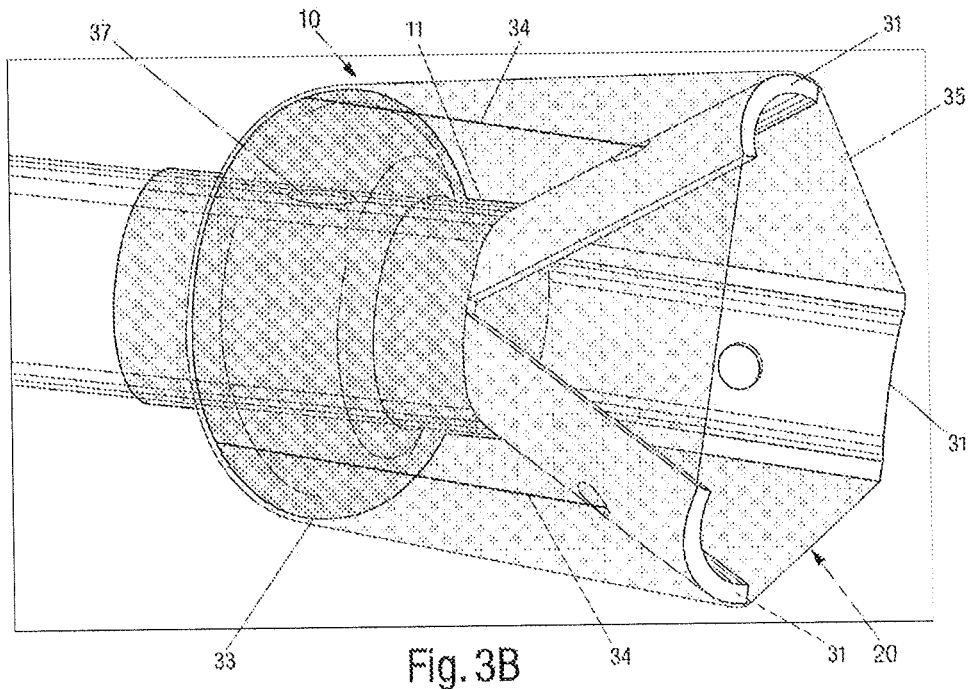

In another embodiment, looking now at FIGS. 3A-B, funnel 20 located at distal end 11 of cannula 10 may be created by providing a plurality of independent strips 31, each coupled at one end to distal end 11 of cannula 10. In the embodiment shown in FIG. 3A, three strips 31 are illustrated. However, it should be appreciated that two or more strips 31 may be used, if so desired. Strips 31, in an embodiment, may be designed to pivot between a closed position, where strips 31 may be substantially adjacent one another, and an open position, where strips may be flared into a funnel 20, shown in FIG. 3A. To deploy strips 31, and thus funnel 20, between an open and closed position, cannula 10 may include a balloon 33 positioned circumferentially about cannula 10 and proximal to strips 31. In addition, an attachment mechanism, such as a string 34 or any similar mechanisms (e.g., rod, chain etc.), may be provided for each of the strips 31, with one end attached to one strip 31 and an opposite end attached to balloon 33. In this way, when balloon 33 is inflated and expands radially, balloon 33 may pull on each attachment mechanism 34, so as to deploy strips 31 into a flared open position. Balloon 33, in one embodiment, may be inflated through opening 37 through the use of any fluid, including water, air, or radioopaque contrast material. It should be noted that securing of the attachment mechanism to the strips 31 and balloon 33 can be accomplished using any methods or mechanisms known in the art. For instance, adhesives, knots, or soldering etc. may be used. Moreover, to the extent desired, ships 33 and balloon 31 may be designed to expand to a diameter larger than that of the vessel within which cannula 10 is being deployed. In that way, cannula 10 may be securely positioned at the site of interest for removal of the undesirable material substantially en bloc.

To better capture the undesirable material and direct it into the cannula 10, a membrane 35 may be placed across a space between adjacent strips 31 when the strips 31 are in the open position. In one embodiment, a continuous membrane 35 may be used to circumferentially stretch across each of the space between adjacent strips 31. Membrane 35 may also act to enhance suction at the site of interest, as it can cover up any open space between the strips 31. To that end, membrane 35, in an embodiment, may be made from a non-permeable material. It should be appreciated that membrane 35 and strips 31, as illustrated, together define funnel 20 at distal end 11 of cannula 10.

Furthermore, to protect the vessel from irritation or damage that may be caused by the presence of balloon 33 and/or strips 31, jacket 36, as shown in FIG. 3B, may be provided circumferentially about the distal 11 of cannula 10. In an embodiment, jacket 36 may extend substantially from a tip of each strip 31 to balloon 33. Jacket 36, however, can be affixed anywhere along each strip 31, if necessary. Since jacket 36 attaches at one end to strips 31 and at an opposite end to balloon 33, jacket 36, in an embodiment, may be used instead of attachment mechanism 34 to deploy strips 31 into an open position when balloon 33 is expanded. Of course, jacket 36 may also be used in conjunction with attachment mechanism 34 to deploy strips 31 into an open position. Furthermore, in one embodiment, jacket 36 may be lengthened, so that the end connected to strips 31 may instead be pulled over strips 31, into funnel 20, and attached substantially to a base of each strips 31 (i.e., base of funnel 20). With such a design, membrane 35 may not be necessary, as jacket 36 may serve the purpose of membrane 35 to cover the space between each of strips 31. In such an embodiment, at least that portion of jacket 36 extending over strips 31 and into the base funnel 20 can be impermeable.

In certain instances, balloon 33 may act to enhance the suction force being applied at the site of interest when removing the undesirable material. For instance, when cannula 10 is deployed downstream of the undesirable material, rather than substantially adjacent to the undesirable material, within a vessel having a venous circulation (i.e., flow toward the heart), balloon 33, when expanded radially, can substantially occlude the vessel, such that collateral fluid flow within the vessel can be minimized, thereby increasing the suction force that can be applied to the undesirable material. Additionally, the occlusion of such a vessel by balloon 33 can better direct the material being removed into the funnel 20 and prevent the material from being carried by the flow of blood past the funnel.

Alternatively, when cannula 10 is deployed upstream of the undesirable material within a vessel having an arterial circulation (i.e., flow away from the heart), rather than substantially adjacent to the undesirable material, balloon 33, when expanded radially, can substantially occlude the vessel, such that pressure being exerted on the downstream material by the fluid flow can be lessened. By lessening the pressure on the material to be removed, the suction force being applied at the site of interest can act to remove the material more easily.

Figures 4A, 4B:
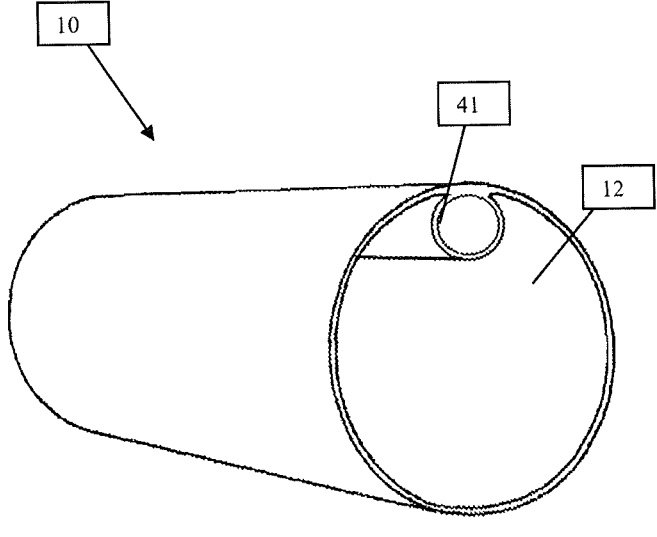
FIGS. 4A-E illustrate a variety of cannulas for use in connection with the system shown in FIG. 1.

As suction cannula 10 may be made from a pliable material, in order to efficiently direct it along a vessel to the site of interest, cannula 10 may be reinforced with wire or other material to optimize maneuverability within the vessel without kinking. Referring now to FIG. 4A, suction cannula 10 may, in addition to pathway 12, be provided with one or more additional pathway or lumen 41. In this multi-lumen design, pathway 12 may act, as noted above, to provide a passage along which the captured material may be transported and directed away from the site of interest. Lumen 41, on the other hand, can provide a passage along which a fluid can be directed to inflate balloon 33 through opening 37 (FIGS. 3A-B). In certain embodiments, lumen 41 may also be used to accommodate other devices, such as other catheters or surgical instruments, for use in connection with a variety of purposes. For example, a device may be inserted and advanced along lumen 41 through the distal end 11 of suction cannula 10 to dislodge the undesirable material. An angiography catheter can be inserted and advanced along lumen 41 through the distal end 11 of suction cannula 10 to perform an angiogram to confirm the location of the undesirable material or confirm that it has been successfully removed. A balloon embolectomy catheter can be inserted along lumen 41 toward the distal end 11 of suction cannula 10 to remove any material which may have clogged the cannula or past the any undesirable material firmly lodged in the vessel to draw it into the cannula. Although illustrated with such a multi-lumen design, any other multi-lumen design may be possible.

Figure 5:
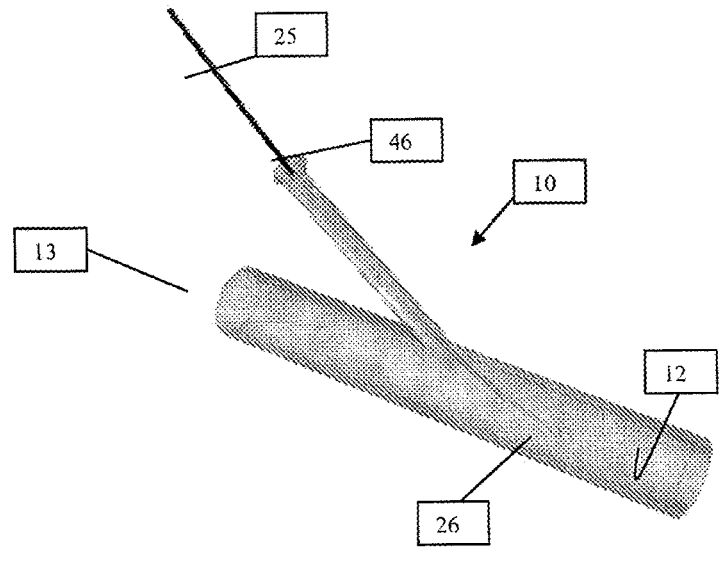
FIG. 5 illustrates a port through which another device may be introduced within a suction cannula used in connection with the system shown in FIG. 1.

To introduce other devices, such as catheter 25 with balloon 26, into lumen 41 or pathway 12, cannula 10 may be provided with a port 51, as shown in FIG. 5, located at the proximal end 13 of cannula 10. It should be appreciated that in the embodiment where cannula 10 has only pathway 12 (i.e., single lumen cannula), port 51 may similarly be provided at the proximal end 13 of cannula 10 to allow the introduction of other devices into pathway 12.

Cannula 10 of the present invention may be of any sufficient size, so long as it can be accommodated within a predetermined vessel, such as a medium to large size blood vessel. The size of cannula 10 may also be determined by the size of the undesirable material to be removed, so long as the undesirable material can be removed substantially en bloc without significant fragmentation. In one embodiment, suction cannula 10 may be designed to remove at least 10 cm³ of undesirable material substantially en bloc. Of course, cannula 10 can be scaled and adapted for use within smaller vessels in the body and for removing a relatively smaller volume or amount undesirable material, if so desired.

Looking again at FIG. 1, system 1 can also include filter device 14 in fluid communication with the proximal end 13 of cannula 10. Filter device 14, in one embodiment, may include an inlet 141 through which fluid removed from the site of interest along with the captured undesirable material can be directed from cannula 10. Filter device 14 may also include an outlet 142 through which filtered fluid from within device 14 may be directed downstream of system 1. To prevent the undesirable material captured from the site of interest from moving downstream of system 1, filter device

14 may further include a permeable sheet 143 positioned within the fluid flow between the inlet 141 and the outlet 142.

Permeable sheet 143, in an embodiment, may include a plurality of pores sufficiently sized, so as to permit fluid from the site of interest to flow therethrough, while preventing any undesirable material captured from the site of interest from moving downstream of system 1. Examples of permeable sheet 143 includes coarse netting, fine netting, a screen, a porous filter, a combination thereof, or any other suitable filter material capable of permitting fluid to flow through while impeding movement of the captured undesirable material. It should be noted that, rather than just one, a plurality of permeable sheets 143 may be used, Alternatively, one permeable sheet 143 may be folded to provide multiple surfaces, similar to an accordion, for use in connection with filter device 14. By using a plurality of permeable sheets 143 or by folding sheet 143, the number of filtration surfaces through which the fluid must flow increases to enhance filtration and further minimize any occurrence of any undesirable material from moving downstream of system 1.

Although a permeable sheet 143 is described, it should be appreciated that filter device 14 may be of provided with any design capable of entrapping the undesirable material, while allowing fluid to move therethrough. To that end, filter device 14 may include a mechanical trap to remove the undesirable material from the fluid flow. Such a mechanical trap may be any trap known in the art and may be used with or without permeable sheet 143.

Still looking at FIG. 1, system 1 may also be provided with a pump 15 designed to generate negative pressure, so as to create a necessary suction force through cannula 10 to pull any undesirable material from the site of interest. In one embodiment, pump 15 may include an intake port 151 in fluid communication with outlet 142 of filter device 14. Intake port 151, as illustrated, may be designed to receive filtered fluid from filter device 14. Pump 15 may also be designed to generate the positive pressure, so as to create a necessary driving force to direct fluid through exit port 152 and downstream of system 1 for reinfusion of fluid removed from the site of interest back into the body. In an embodiment, the suction force and the drive force may be generated by pump 15 simultaneously and may take place continuously or intermittently for a set duration. Pump 15, as it should be appreciated, may be any commercially available pump, including those for medical applications and those capable of pumping fluids, such as blood. Examples of such a pump includes a kinetic pump, such as a centrifugal pump, and an active displacement pump, such as a rollerhead pump.

In an alternate embodiment, an independent vacuum device (not shown), may be provided for generating the necessary suction force at the site of interest, while a pump 15 may act to generate the necessary driving force for reinfusion purposes. In such an embodiment, pump 15 may be in fluid communication with the filter device 14, while the vacuum device may be in fluid communication with suction cannula 10 upstream to the filter device 14. The independent pump 15 and vacuum device may operate intermittently for a set duration, and if desired, either the vacuum device or pump 15 may operate continuously, while the other operates intermittently.

Downstream of pump 15, system 1 may further include a second or reinfusion cannula 16 in fluid communication with the exit port 152 of pump 15. Reinfusion cannula 16, in an embodiment, may be designed to permit filtered fluid, directed from filter device 14 by way of pump 15, to be reinfused back into a patient at a desired site. To that end, reinfusion cannula 16 may be designed for placement within the same or different vessel within which suction cannula 10 may be located.

Reinfusion cannula 16, in one embodiment, may be an elongated tube and includes a distal end 161 through which cleansed or filtered fluid can be reinfused back into the body. In an embodiment, distal end 161 of reinfusion cannula 16 may be designed so that it can be situated in spaced relation to the distal end 11 of the suction cannula 10 when system 1 is in operation. Reinfusion cannula 16 may also include a lumen or pathway 162 extending along its body portion to provide a passage along which the filtered fluid, such as blood, may be transported to a reinfusion site. Reinfusion cannula 16 may further include a proximal end 163 in opposing relations to the distal end 161, and through which the filtered fluid from pump 15 may enter into the cannula 16.

Furthermore, similar to suction cannula 10, since reinfusion cannula 16 may be designed for introduction into the vasculature, and may need to be maneuvered therealong, reinfusion cannula 16, in one embodiment, may be made from a pliable material. In one embodiment, reinfusion cannula 16 may be constructed from a biocompatible material, such as polyvinyl chloride, polyethylene, polypropylene, polyurethane, polyether block amide (Pebax®), silicone, or a combination thereof. In certain instances, it may be desirable to maneuver reinfusion cannula 16 to the reinfusion site using image guidance, for example, using fluoroscopy or echocardiography. To permit reinfusion cannula 16 to be visualized, reinfusion cannula 16, in an embodiment, may also be made to include a radioopaque material.

Since reinfusion cannula 16 may be made from a pliable material, in order to efficiently direct it along a vessel to the reinfusion site, reinfusion cannula 16 may be reinforced to optimize maneuverability within the vessel without kinking. Moreover as shown in FIG. 4B, reinfusion cannula 16 may be provided with one or more additional lumens. With a multi-lumen design, lumen 162, as noted above, may act to provide a passage along which the filtered fluid may be transported and directed to the reinfusion site. Lumen 42, on the other hand, can provide a passage through which a guide wire can be inserted to assist in the guiding the reinfusion cannula 16 to the reinfusion site, or through which other instruments and devices may be inserted for various surgical procedures. With such a multi-lumen design, reinfusion cannula 16 can serve as an introducer sheath by providing lumen 42 through which these instruments can pass, while filtered blood can be reinfused through lumen 162. Although illustrated with such a multi-lumen design, any other multi-lumen design may be possible.

Figure 4C:
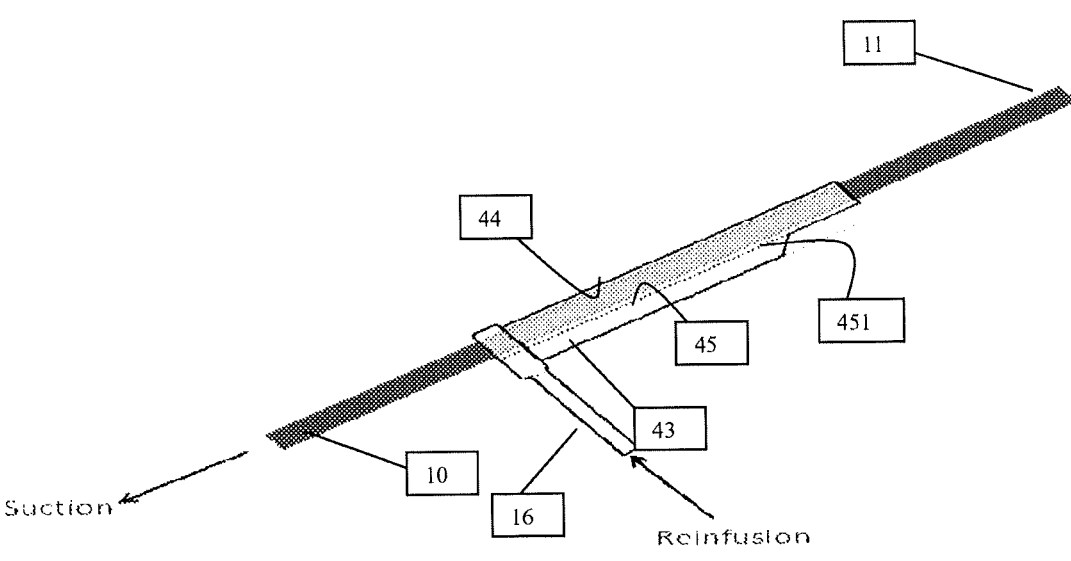

Although illustrated as a separate component from suction cannula 10, in certain embodiments, the reinfusion cannula 16 may be designed to be substantially integral with suction cannula 10. In one embodiment, as illustrated in FIG. 4C, reinfusion cannula 16 may be incorporated as part of a double or multi-lumen introducer sheath 43 for insertion into the same vessel within which the suction cannula 10 may be situated. In particular, suction cannula 10 may be inserted and maneuvered through one lumen 44 of sheath 43, while reinfusion cannula 16 may be in fluid communication with lumen 45 of sheath 43. In such an embodiment, lumen 45 may include a distal end 451 in spaced relations to the distal end 11 of cannula 10, so that cleansed or filtered fluid may be introduced to the reinfusion site away from the site of interest where the distal end 11 of cannula 10 may be positioned.

Figure 4D:
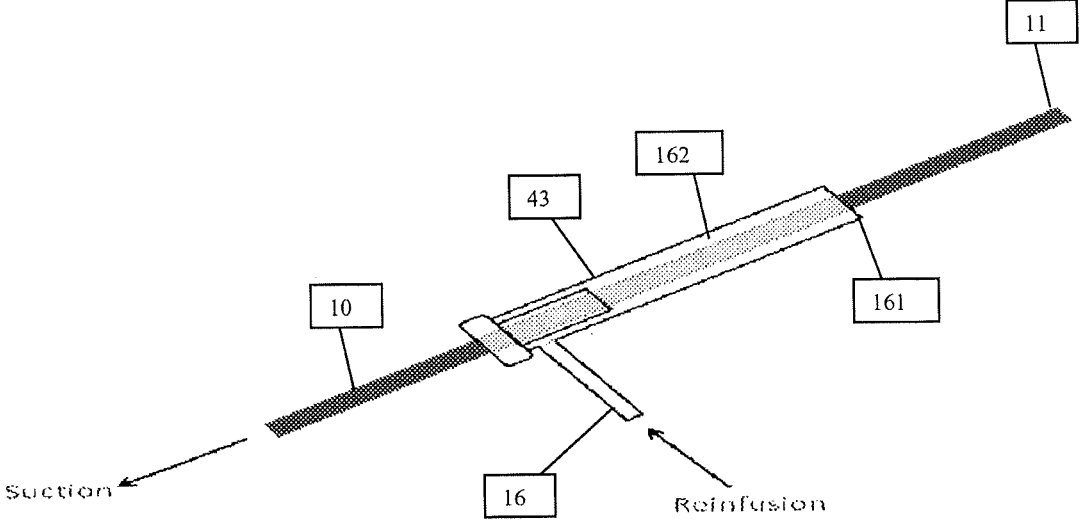

Alternatively, as illustrated in FIG. 4D, reinfusion cannula 16 may be incorporated as part of a double or multi-lumen introducer sheath 43 where the reinfusion cannula 16 and the suction cannula 10 may be concentrically aligned along a shared axis A. In the embodiment shown in FIG. 4D, reinfusion cannula 16 may have a diameter that can be relatively larger than that of suction cannula 10. To that end, reinfusion cannula 16 can accommodate suction cannula 10 within pathway 162 of the reinfusion cannula 16, and allow suction cannula 10 to extend from within pathway 162, such that the distal end 11 of suction cannula 10 may be positioned in spaced relations relative to the distal end 161 of reinfusion cannula 16. The spaced relations between distal end 161 and distal end 11 allows filtered fluid to be introduced to the reinfusion site away from the site of interest, where the removal of the undesirable material may be occurring.

Figure 4E:
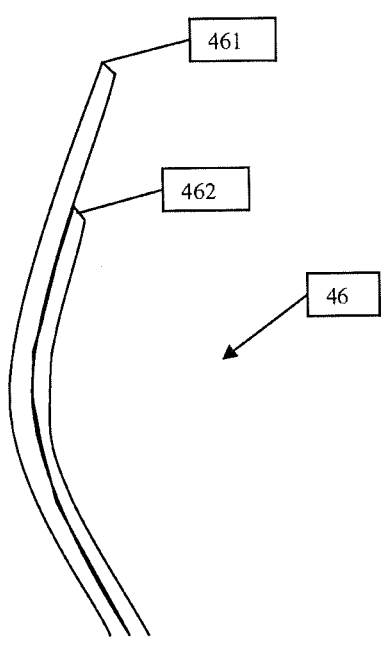

In another embodiment, reinfusion cannula 16 and suction cannula 10 can be integrated into a single multi-lumen suction-reinfusion cannula 46, as shown in FIG. 4E. In the embodiment shown in FIG. 4E, multi-lumen cannula 46 may include a distal suction port 461 through which undesirable material from the site of interest can be removed, and a proximal reinfusion port 462 through which cleansed or filtered fluid may be reinfused back into the body. The spaced relations between the suction port 461 and reinfusion port 462 allows filtered fluid to be introduced to the reinfusion site away from the site of interest where the removal of the undesirable material may be occurring.

In an embodiment, the size of the reinfusion cannula, whether independent from the suction cannula, part of a multi-lumen introducer sheath, part of a multi-lumen combined suction-reinfusion cannula, or in concentric alignment with the suction cannula, may be designed so that it can handle a relatively rapid reinfusion of large volumes of fluid by pump 15.

Figure 6:
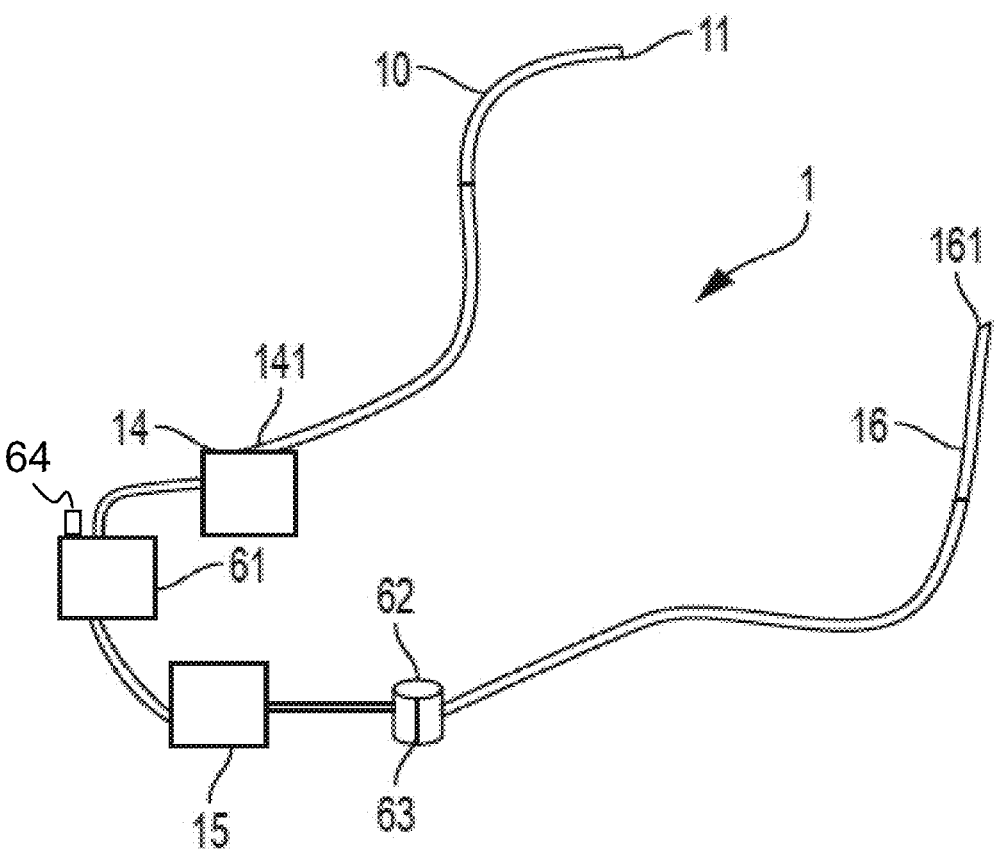
FIG. 6 illustrates a system for removing an undesirable material from within a vessel in accordance with another embodiment of the present invention.

With reference now to FIG. 6, system 1 may also include a reservoir 61. Reservoir 61, in one embodiment, may be situated in fluid communication between filter device 14 and pump 15, and may act to transiently collect fluid filtered from the site of interest, prior to the filtered fluid being directed into reinfusion cannula 16. By providing a place to transiently collect fluid, reservoir 61 can allow the rate of suctioning (i.e., draining, aspirating) to be separated from rate of reinfusing. Typically, the rate of reinfusion occurs at substantially the same rate of suctioning, as the volume of fluid suctioned from the site of interest gets immediately directed along the system 1 and introduced right back to the reinfusion site in a patient. However, the availability of a volume of transiently collected fluid in reservoir 61 now provides a source from which the amount or volume of fluid being reinfused back into the patient can be adjusted, for example, to be less than that being suctioned from the site of interest, as well as the rate at which fluid can be reinfused back into the patient, for example, at a relatively slower rate in comparison to the rate of suctioning. Of course, if so desired or necessary, the reinfusion rate and volume can be adjusted to be higher, relative to the rate and volume of suction.

In accordance with one embodiment of the present invention, reservoir 61 may be a closed or an open container, and may be made from a biocompatible material. In an embodiment where reservoir 61 may be a closed container, system 1, likewise, will be a closed system. As a result, pump 15 may be used as both a suction source and a driving force to move fluid from the site of interest to the reinfusion site. In such an embodiment, pump 15 can generate a suction force independently of or alternately with a driving force to allow reservoir 61 collect filtered fluid from filter device 14. In one embodiment, pump 15 may be provided with a gauge in order to measure a rate of flow of the fluid being reinfused.

Alternatively, where reservoir 61 may be an open container, reservoir 61, in such an embodiment, may be designed to accommodate both a volume of fluid, typically at the bottom of reservoir 61, and a volume of air, typically at the top of reservoir 61, to provide an air-fluid interface within reservoir 61, with a port or venting aperture 64 therein to vent air from reservoir 61. As a result, using pump 15 in fluid communication with reservoir 61 may not provide the needed driving force and/or suction force to adequately remove the undesirable material and to subsequent reinfuse fluid back into a patient. To address this, system 1, in an embodiment, may include a separate and independent vacuum source, in fluid communication with the volume of air at the top of reservoir 61, for providing the necessary suction force from the top area of reservoir 61 where air exists, through filter device 14, through the distal end 11 of cannula 10, and to the site of interest. A port provided above the fluid level within reservoir 61 may be provided to allow the independent vacuum source to be in fluid communication with the volume of air within reservoir 61. Pump 15, on the other hand, may be in fluid communication with the volume of fluid within reservoir 61, and may act to generate the necessary driving force for reinfusion purposes.

It should be appreciated that although shown as separate components, to the extent desired, reservoir 61 and filter device 14 may be combined as a single unit.

Still referring to FIG. 6, system 1 may further include a second filter device 62 positioned in fluid communication between pump 15 and reinfusion cannula 16. Second filter device 62 may act to remove any debris or material (e.g., ranging from smaller than microscopic in size to relatively larger) that may have escaped and moved downstream from filter device 14, so that the fluid may be substantially cleansed prior to reinfusion. In an embodiment, second filter device 62 may include a porous membrane 63 whose pores may be measurably smaller than that in filter device 14, but still capable of allowing fluid to flow therethrough.

Since fluid such as blood needs to be filtered through system 1, it should be noted that system 1 and its components may be made from a biocompatible material to minimize any adverse reaction when fluid removed from the site of interest gets reinfused back into the body.

In operation, system 1 of the present invention may be introduced into the vasculature, preferably through a peripheral blood vessel, to remove undesirable material, such as a clot, emboli, or thrombi, substantially en bloc and without significant fragmentation, and subsequently reinfusing fluid removed from the site of interest back into a patient. In particular, system 1 and its components disclosed above can collectively form a substantially closed circuit through which fluid and an undesirable material from a site of interest can be removed by suction, cleared of the undesirable material, filtered to remove any additional debris, and actively introduced back into a patient at a reinfusion site.

Figure 7:
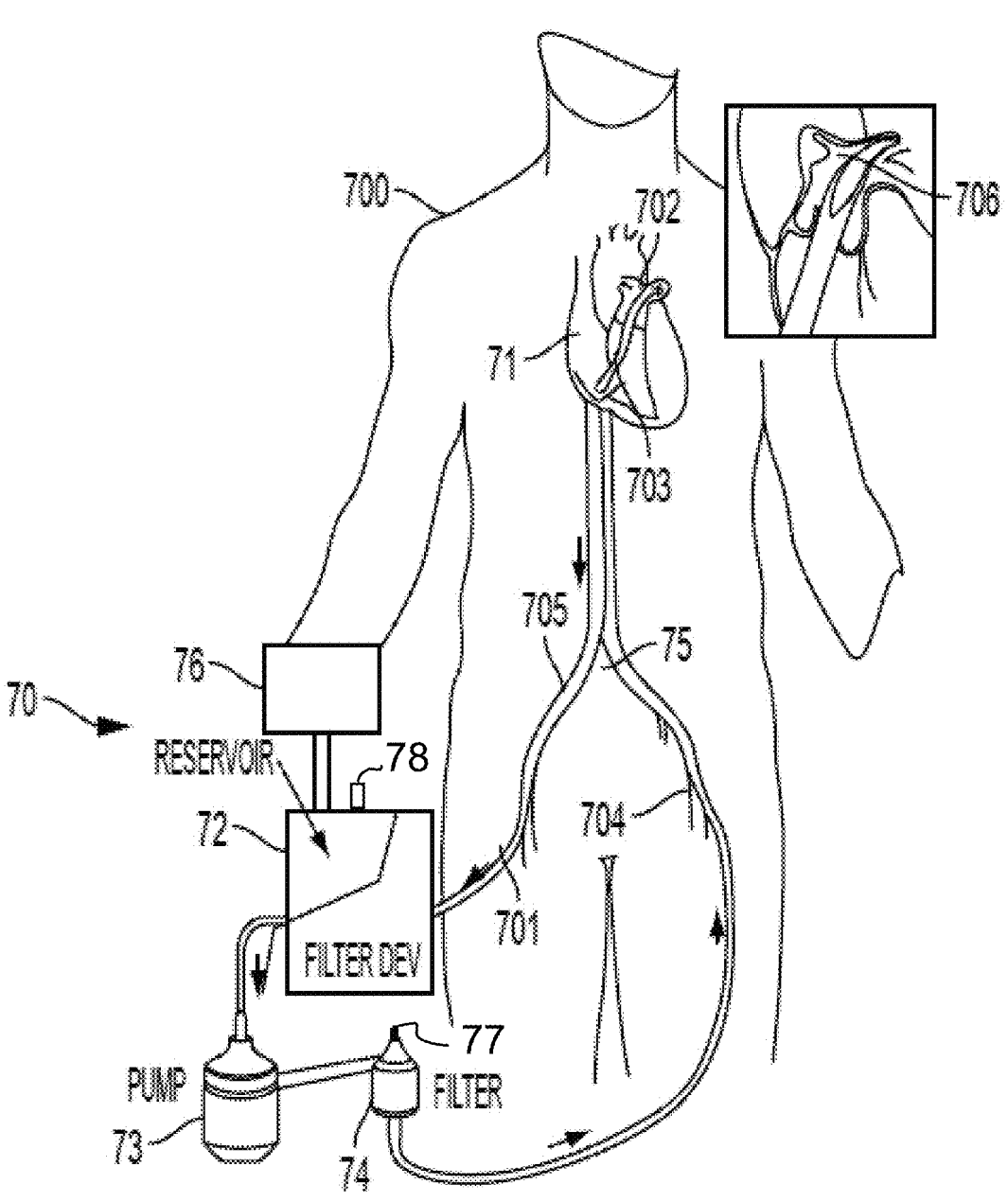
FIG. 7 illustrates a system of the present invention being deployed within a patient for removing an undesirable material from a site of interest.

With reference now to FIG. 7, there is shown one embodiment of the system of the present invention being utilized for removal of an undesirable material within a patient 700. System 70, as illustrated, includes a suction cannula 71, filter device 72, pump 73, second filter device 74 and reinfusion cannula 75. It should be appreciated that depending on the procedure and to the extent desired, system 70 may not need all of the components shown, or may need other components in addition to those shown.

In general the method of the present invention, in one embodiment, includes, initially accessing a first blood vessel 701 either by surgical dissection or percutaneously with, for instance, a needle and guide wire. The first blood vessel through which suction cannula 71 may be inserted into patient 700 can be, in an embodiment, any blood vessel that can be accessed percutaneously or by surgical dissection such as femoral vein, femoral artery or jugular vein. Next, suction cannula 71 may be inserted into the first blood vessel 701 over the guide wire, and advanced toward a site of interest 702, for instance, in a second vessel or a heart chamber 703 where an undesirable material 706 may be residing, The second blood vessel or heart chamber, in an embodiment, can be the main pulmonary artery, branch pulmonary arteries, inferior vena cavae, superior vena cavae, deep veins of the pelvic, legs, arms or neck, aorta, or any other medium to large blood vessel for which the use of a cannula is suitable for removing undesirable material without causing undesirable damage to the blood vessel. In addition, the advancement of suction cannula 71 may be gauged or documented by fluoroscopic angiography, echocardiography or other suitable imaging modality.

In the case of pulmonary embolism, the suction cannula 71 may normally be introduced through the femoral, jugular or subclavian vein, Alternatively, the suction cannula 71 may be introduced, if desired, directly into the cardiac chambers using a minimally invasive surgical or endoscopic, thoracoscopic, or pericardioscopic approach.

Thereafter, a third blood vessel 704 may be accessed either by surgical dissection or percutaneously with, for example, a needle and guide wire. Subsequently, reinfusion cannula 75 may be inserted into the third blood vessel 703 using an open or over the guide wire technique. The third blood vessel through which the reinfusion cannula 75 may be inserted, in one embodiment, can be any large vein, such as the femoral vein or jugular vein. Reinfusion cannula 75 may then be advanced toward a reinfusion site, for example, within a fourth blood vessel 705. The fourth blood vessel, in one embodiment, can be the femoral vein, iliac vein, inferior vena cava, superior vena cava or right atrium.

Once reinfusion cannula 75 is in place and components of system 70 have connected, pump 73 may be activated, and suction cannula 71 may then be placed against and in substantial engagement with the undesirable material 706 at the site of interest 702 for removal by suctioning through the suction cannula 71. The undesirable material 706 and circulatory fluid removed from the site of interest 702 may thereafter be directed along suction cannula 71 into filter device 72 where the undesirable material 706 can be entrapped and removed from the fluid flow. The resulting filtered fluid may next be directed downstream by way of pump 73 into the second filter device 74, where any debris or material (e.g., ranging from smaller than microscopic in size to relatively larger) that may have escaped and moved downstream from filter device 74 can be further captured and removed from the fluid flow prior to reinfusion. The resulting cleansed fluid may then be directed into the reinfusion cannula 75 and introduced back into the patient 700.

It should be appreciated that in certain instances, prior to connecting the suction cannula 71 and the reinfusion cannula 75, system 70 may need to be primed with fluid to minimize or eliminate any air and/or air bubbles from the system prior to the initiation of suction and reinfusion. To that end, the suction cannula 71 and reinfusion cannula 75 can be primed separately with fluid or by allowing blood to backfill the cannulae after insertion. The remaining components of the system 70 including all tubing, the filter device 72, the pump 73 and any other components of system 70 may also need to be primed with fluid prior to connecting them to the cannulae. In one embodiment, this can be achieved by temporarily connecting these components in fluid communication with one another as a closed circuit and infusing fluid through a port, similar to port 51 in FIG. 5, while providing another port or venting aperture 77 (or ports 64, 78) through which air can be displaced. Once these components have been fully primed with fluid, the circuit can be detached and connected to the primed suction cannula 71 and reinfusion cannula 75 in the appropriate configuration. Examples of a priming fluid include crystalloid, colloid, autologous or heterologous blood, among others.

During operation, pump 73, in one embodiment, may remain activated so that suction and continuous reinfusion of blood can occur continuously for a desired duration or until the removal of the undesirable material has been confirmed, for instance, by visualizing the captured undesirable material in the filter device 72. Alternatively pump 73 can be activated intermittently in short pulses, either automatically or manually by an operator (e.g., surgeon, nurse or any operating room attendant), for a desired duration or until the removal of the undesirable material has been confirmed by visualization of the material within filter device 72.

It should be appreciated that since suction cannula 71 may be deployed within any vessel within patient 700, depending on the procedure, in addition to being placed substantially directly against the undesirable material at the site of interest, suction cannula 71 may be deployed at a location distant from the site of interest where direct engagement with the undesirable material may not be possible or desired.

In a situation where the suction cannula 71 is positioned within a vessel exhibiting a venous flow and at a distant location from the undesirable material, it may be desirable to place the distal end of suction cannula 71 downstream of the undesirable material, so that the fluid flow can push the undesirable material from the site of interest into suction cannula 71 during suction. To the extent there may be some difficulties with suctioning the undesirable material from its location, if necessary, a catheter may be deployed through suction cannula 71 and to the site of interest, where the undesirable material may be dislodged location for subsequent removal.

On the other hand, when suction cannula 71 is positioned within a vessel exhibiting arterial flow and at a distant location from the undesirable material, it may be necessary to place the distal end of suction cannula 71 upstream of the undesirable material for the purposes of removal, even though the undesirable material must move against the fluid flow in order to enter into the suction cannula 71. In such a situation, since the fluid flow in the vessel tends to exert a pressure against the undesirable material at the site of interest, and thus may make the undesirable material difficult to remove, suction cannula 71 may include a flow occlusion mechanism, similar to balloon 33 shown in FIG. 3. When expanded radially, the mechanism can substantially occlude the vessel, such that pressure being exelied on the downstream material by the fluid flow can be lessened. By lessening the pressure on the undesirable material to be removed, the suction force being applied at the site of interest can act to remove the material more easily. Again, if necessary, a catheter may be deployed through suction cannula 71 and to the site of interest, where the undesirable material may be dislodged or drawn back into the cannula to facilitate its removal.

The method of the present invention may also utilize a fluid reservoir, having a port or venting aperture 78 for displacing air, similar to reservoir 61 shown in FIG. 6, in connection with system 70. Such a reservoir may be placed in fluid communication between filter device 72 and pump 73. The reservoir, in an embodiment, may be an independent reservoir or may be integrated with filter device 72 as a single unit, similar to that shown in FIG. 7. By utilizing a reservoir, a volume of transiently collected fluid may be used to independently control the rate or volume of suctioning (i.e., draining, aspirating) and/or the rate or volume of reinfusion.

In an embodiment where the reservoir may be an open container, it should be appreciated that system 70 may not be a substantially closed system. As a result, rather than utilizing a pump that can generate both a suction and a driving force for a closed system, an independent vacuum device 76 may be employed to generate the necessary suction force, from the top of the reservoir where a volume of air exists, for removal of the undesirable material, while independent pump 73 may be employed to generate the necessary driving force, from the bottom of the reservoir where a volume of aspirated fluid exists, for reinfusion.

The method of the present invention may also utilize a suction cannula 71 with a deployable funnel tip, similar to funnel 20 in FIG. 2 or in FIG. 3. In such an embodiment, the funnel may be deployed after suction cannula 71 has been positioned adjacent the site of interest. Thereafter, once the suction force has been activated, the funnel may be advanced to engage the undesirable material for removal. The funnel may remain deployed while the suction force is activated, and through multiple cycles, if necessary, until the undesirable material can be removed. Subsequently, the funnel may be retracted in order to reposition or remove suction cannula 71.

The method of the present invention may further utilize reinfusion cannula 75 that has been incorporated into an introducer sheath, such as sheath 43 as a multi-lumen cannula (FIG. 4C) or as one which concentrically aligns the suction cannula and reinfusion cannula (FIG. 4D), In this embodiment, the sheath/reinfusion cannula 75 may initially be inserted into a first blood vessel. Suction cannula 71 may then be inserted into the introducer lumen of the sheath/reinfusion cannula 75, and the assembly advanced together to a site of interest in a second blood vessel or heart chamber.

The method of the present invention may also further utilize a combined multi-lumen suction/reinfusion cannula, similar to cannula 46 shown in FIG. 4E, In such an embodiment, the combined suction/reinfusion cannula may initially be inserted into a first blood vessel to a location where its distal suction lumen can be placed adjacent the site of interest within a second blood vessel, while its proximal located reinfusion lumen can be positioned at an appropriately spaced location from the suction lumen.

The method of the present invention may, in an embodiment, be employed to remove a plurality of undesirable materials, for instance, within the same vessel or its branches, from multiple vessels within the same vascular bed (e.g. left and right pulmonary arteries), from different vascular beds (e.g. pulmonary altery and iliofemoral veins), or a combination thereof. In such an embodiment, after the first undesirable material has been removed, the suction force may be deactivated. The next undesirable material to be removed may then be located, for example, using an appropriate imaging modality. Suction cannula 71 may thereafter be advanced to the location of this second undesirable material, and the suction force reactivated as above until this second undesirable material may be removed. The cycle may be repeated until each undesirable material at the various identified locations has been removed. Once all undesirable material has been removed, an appropriate procedure to prevent the development of or migration of new material, such as placement of an inferior vena cava filter, may be performed.

The method of the present invention may also be employed in combination with a balloon embolectomy catheter or other devices suitable for dislodging clots or other undesirable material from a cannula or a vessel. For example, should an undesirable material be lodged within suction cannula 71, a balloon catheter can be inserted through, for instance, a side port, similar to port 51 in FIG. 5, of suction cannula 71 and advanced past the lodged undesirable material. The balloon catheter may subsequently be inflated distal to the undesirable material. Once inflated, the suction force may be activated and the inflated catheter withdrawn along the suction cannula 71 to dislodge the undesirable material from its location of obstruction. In a situation where the undesirable material may be adherent to a vessel wall, or for some other reason cannot be dislodged by simply applying suction to the site of interest, the balloon catheter can be inserted through the side port of suction cannula 71, advanced past a distal end of cannula 71, and past the adherent undesirable material. The balloon catheter may then be inflated distal to the undesirable material. Once inflated, the suction force may be activated and the inflated catheter withdrawn along the suction cannula 71. As it is withdrawn, the balloon catheter can act to drag the undesirable material into suction cannula 71.

In some cases, a vegetative growth may become dislodged during a surgical procedure. An infective vegetative growth may grow within a patient's heart especially if, for example, there is some abnormality in the heart. Vegetative growths have been known to grow at a site where a pacemaker lead is attached to the heart, in or around artificial heart valves, and in or around abnormal heart valves.

During a surgical procedure, the vegetative growths in and around the heart may become dislodged. For example, a vegetative growth that has grown on a pacemaker lead in the heart may become dislodged when the pacemaker lead is removed during a surgical procedure. The vegetative growth may become dislodged naturally when the lead is removed, or may be manually removed by the surgeon. Similarly, vegetative growths in and around artificial or abnormal heart valves may become dislodged during a surgical procedure performed on or near the heart valves.

Dislodged vegetative growths that make their way into the circulatory system can become emboli and cause serious health problems. If a vegetative growth becomes lodged in an area of the circulatory system, it can cause complications such as stroke, heart attack, pulmonary embolisms, etc.

The systems and methods of the present invention, in some embodiments, may be implemented within a patient during a surgical procedure in order to protect the patient from complications caused by dislodged vegetative growth. For example, the present invention may be used to capture dislodged vegetative material during a surgical procedure so that the vegetative growth does not become lodged in another area of the circulatory system where it can create a blockage. In particular, as illustrated by FIG. 7, during a surgical procedure, such as the removal of a pacemaker lead from the heart, suction cannula 71 may be placed in a strategic location where it can capture vegetative material that may become dislodged during removal of the pacemaker lead.

Suction cannula 71, in one embodiment, may be placed at a strategic location within the circulatory system so that any vegetative growth that is dislodged, in whole or in part, during surgery is likely to be captured and removed by suction cannula 71 before it can cause a blockage or other complications for the patient. In some cases, suction cannula 71 may be placed downstream of the vegetative growth so that, if the vegetative grown becomes dislodged during surgely, it will travel with the flow of blood toward suction cannula 71, For example, if the vegetative growth has formed on a pacemaker lead in the right ventricle, suction cannula 71 may be placed within the right ventricle adjacent to the vegetative growth, near or around the pulmonary valve, or in the pulmonary arteries so that the flow of blood through the heart can carry the vegetative growth from the right ventricle toward suction cannula 71. Of course, the suction force provided by suction cannula 71 may also help to direct the dislodged vegetative growth toward suction cannula 71, as described above.

One skilled in the art will recognize that suction cannula 71 may be placed at other strategic locations depending upon the particular surgery performed and the location of the vegetative growth. For example, if the vegetative growth is located within the left atrium, suction cannula 71 may be placed at any location downstream of the vegetative growth, including, but not limited to: the left atrium, on or around the mitral valve, the left ventricle, on or around the aortic valve, the aorta, etc. In some embodiments, suction cannula 71 may be placed at a strategic location upstream of the vegetative growth if suction cannula 71 is likely to capture dislodged vegetative growth when placed at the upstream location.

Reinfusion cannula 16 may also be positioned within the circulatory system during the surgical procedure. Reinfusion cannula 16 may be, for example, placed at a position such that the distal end of reinfusion cannula 16 is in a spaced relation to the distal end of suction cannula 71. In one embodiment, reinfusion cannula 16 may be placed within the circulatory system at a distance from suction cannula 16. Alternatively, it may be placed near suction cannula 16. As discussed above, reinfusion cannula 16, when active, may return blood and other fluid to the body after it has been removed by suction cannula 71. Because the normal rate of blood flow through the heart and large blood vessels can be significant, suction cannula 11 and reinfusion cannula 16, when used around the heart and other large vessels, may displace a relatively large volume of fluid into and out of the patient's circulatory system.

Once positioned at the desired strategic location, suction cannula 71 may be engaged to apply a suction force to the area of interest and reinfusion cannula 16 may be engaged to return fluids to the body. Suction cannula 71 and reinfusion cannula 16 may remain engaged for the duration of the surgical procedure, or during part of the surgical procedure, in order to protect the patient by capturing any vegetative material that becomes dislodged during the surgical procedure. One skilled in the art will recognize that, when engaged, suction cannula 71 by design may capture dislodged vegetative material en bloc, may capture parts or fragments of a vegetative growth that become dislodged, and may capture any other debris that becomes dislodged during surgery.

In other cases, suction cannula 71 and/or reinfusion cannula 16 may be used to directly dislodge the vegetative growth. In such an embodiment, the suction force and/or the reinfusion of fluid provided by suction cannula 71 and reinfusion cannula 16, if engaged directly onto the vegetative growth, may be sufficient to dislodge the vegetative growth from its position within or near the heart. In other cases, an external force may assist in dislodging the vegetative growth. For example, a catheter extended from a lumen in suction cannula 71 and/or reinfusion cannula 16 may be used to physically dislodge or loosen the vegetative growth and remove it from its location for subsequent capture by suction cannula 71. A device for dislodging or breaking up the vegetative growth may be attached to the catheter. Such devices may include balloons, aspiration devices, rheolytic devices, fragmentation devices, etc. In other cases, suction cannula 71 and/or reinfusion cannula 16 may be used to scrape the vegetative growth from its location, thus dislodging the vegetative growth for capture by suction cannula 71.

The method of the present invention may further be employed in combination with a distal protection device (not shown), such as a netting device, designed to be positioned downstream of the undesirable material, when removal may be performed within a vessel having arterial flow. In particular, with suction cannula 71 positioned upstream of the undesirable material, the netting device may be inserted through a side port in suction cannula 71, advanced past the undesirable material to a downstream location. The netting device may then be deployed to an open position approximating the diameter of the vessel. The deployed netting device may then act to entrap any material that may be dislodged from the site of interest and pushed downstream by the fluid flow. In the absence of the netting device, a dislodged material may be pushed downstream and may be lodged in a more life threatening location.

It is evident from the above description that the systems, including the various components, and methods of the present invention can act to remove clots and other types of undesirable material from the circulation, particularly from medium to larger vessels and heart chambers. Important to achieving this includes the ability of the operator to perform substantially en bloc removal of the undesirable material without significant fragmentation from the site of interest. Such a protocol may only be achieved previously with invasive, open surgery. In addition, by providing a system with components to permit aspirated fluid from the site of interest to be reinfused back to the patient, the system of the present invention allows a sufficiently and relatively large suction cannula to be employed for the removal of a relatively large undesirable material 15 in substantially one piece, without fragmentation. Furthermore, by providing a definitive mechanical treatment to the problem, the systems and methods of the present invention provide an attractive alternative to treatments, such as thrombolysis, which may not be an option or may be ineffective for many patients, and which may carry a significant risk of major complications. As such, the systems and methods of the present invention now provide a significant contribution to the field of cardiovascular medicine and surgery, particularly thromboembolic disease.

Although references have been made in connection with surgical protocols, it should be appreciated that the systems and methods of the present invention may be adapted for use in connection with non-surgical protocols, and in connection with any vessel capable of permitting fluid flow therethrough and capable of being obstructed. For instance, the system of the present invention may be adapted for use in connection with clearing obstructed oil pipelines, water pipes, and air ducts, among others.

While the present invention has been described with reference to certain embodiments thereof, it should be understood by those skilled in the art that various changes may be made and equivalents may be substituted without departing from the true spirit and scope of the invention. In addition, many modifications may be made to adapt to a particular situation, indication, material and composition of matter, process step or steps, without departing from the spirit and scope of the present invention. All such modifications are intended to be within the scope of the claims appended hereto.

The invention claimed is:

1. A system for aspirating and filtering undesirable material from a vasculature, the system comprising:
   a cannula comprising a funnel shaped distal end and a lumen, the funnel shaped distal end comprising an expandable reinforcement structure and an impermeable membrane, the impermeable membrane being coupled to the expandable reinforcement structure;
   a pump configured to be operably coupled to the cannula, wherein the pump is configured to create a suction force sufficient to aspirate the undesirable material and blood through the cannula lumen, and the funnel distal end facilitates a vortex flow of the undesirable material and blood within the funnel shaped distal end to facilitate conforming the undesirable material into the cannula lumen; and
   a filter assembly configured to receive the aspirated undesirable material and blood, the filter assembly comprising an inlet, an outlet, a filter membrane, and a fluid path extending from the inlet through the filter membrane and to the outlet, wherein the filter membrane is configured to permit the aspirated blood to flow along the fluid path from the inlet to the outlet and inhibit the aspirated undesirable material from flowing along the fluid path from the inlet to the outlet,
   wherein the filter assembly includes a venting aperture configured to displace air from the filter assembly, the venting aperture being positioned above a fluid level of the filter assembly.

2. The system of claim 1, further comprising an agitator positioned within the funnel shaped distal end to agitate the undesirable material within the funnel shaped distal end.

3. The system of claim 2, wherein the funnel shaped distal end is configured to aspirate the undesirable material substantially en bloc.

4. The system of claim 2, wherein:
   the expandable reinforcement structure is a polymer material; and the expandable reinforcement structure is balloon actuated;
   the expandable reinforcement structure comprises at least two strips; and the pump is an automated pump;
   the agitator is a balloon embolectomy catheter;
   the funnel shaped distal end further comprises a mechanism configured to deploy the expandable reinforcement structure; and
   the pump is configured to generate a drive force simultaneously with the suction force.

5. The system of claim 1, wherein the filter assembly is configured to permit captured undesirable material to be visualized within the filter assembly.

6. The system of claim 1, further comprising another pump, the another pump being a manually operated pump configured to flow the aspired blood and undesirable material along the fluid path within the filter assembly for a desired duration or until the filtered undesirable material has been visually confirmed within the filter assembly.

7. The system of claim 1, wherein a diameter of the funnel shaped distal end is at least three times larger than a diameter of the cannula lumen.

8. The system of claim 1, wherein:

the expandable reinforcement structure further comprises a base and a distal most end;

the impermeable membrane is configured to extend from the expandable reinforcement structure base to the expandable reinforcement structure distal most end;

the funnel shaped distal end further comprises a radiopaque marker; and the impermeable membrane is coupled to either an inner surface of the expandable reinforcement structure, an outer surface of the expandable reinforcement structure, or both the inner surface and the outer surface of the expandable reinforcement structure.

9. The system of claim 1, further comprising:

a first container configured to receive the aspirated undesirable material and blood, the first container is configured to be operably coupled to the filter assembly;

a second container configured to receive the aspirated blood that passed through the filter membrane, the second container is configured to be operably coupled to a reinfusion cannula configured to be placed in the vasculature; and another pump configured to be operably coupled to the reinfusion cannula and configured to generate a reinfusion force sufficient to drive the filtered blood through the reinfusion cannula into the vasculature.

10. The system of claim 9, wherein the filter membrane further comprises a first filter material having a first pore size and a second filter material having a second pore size; the first pore size is different than the second pore size; and the first filter material and the second filter material are configured to minimize any occurrence of the aspirated undesirable material from flowing along the fluid path from the inlet to the outlet.

11. A system comprising:

a cannula comprising an expandable funnel shaped distal end and a lumen, the expandable funnel shaped distal end comprising a reinforcement structure and an impermeable membrane, the impermeable membrane being coupled to the reinforcement structure, and the cannula being configured to be placed into a vasculature;

a manually operated pump configured to be in fluid communication with the cannula, wherein the manually operated pump is configured to create a suction force sufficient to aspirate an undesirable material and blood through the cannula lumen; and a filter assembly configured to receive the aspirated undesirable material and blood, the filter assembly comprising an inlet, an outlet, a first filter membrane, a second filter membrane, and a fluid path extending from the inlet through the first and second filter membranes and to the outlet, wherein the second filter membrane is positioned downstream from the first filter membrane, and the first filter membrane comprises a first filter pore size and the second filter membrane comprises a second filter pore size, the first filter pore size being larger than the second filter pore size, wherein the first and second filter membranes are configured to permit the aspirated blood to flow along the fluid path from the inlet to the outlet and inhibit the undesirable material from flowing along the fluid path from the inlet to the outlet, and wherein the filter assembly is configured to permit the filtered undesirable material to be visualized therein.

12. The system of claim 11, wherein:

the expandable funnel shaped distal end is configured to transition from a compressed state to an expanded state;

the cannula further comprises a cannula reinforcement element;

the reinforcement structure is configured to withstand a negative pressure generated from the suction force and prevent the expandable funnel shaped distal end from unintentionally transitioning from the expanded state to the compressed state; and the cannula reinforcement element is configured to withstand the negative pressure generated from the suction force and prevent the cannula from collapsing.

13. The system of claim 11, further comprising:

a first container configured to receive the aspirated undesirable material and blood;

a second container configured to receive the filtered blood that passed through the first and second filter membranes; and a reinfusion cannula configured to be operably coupled to the second container, placed in the vasculature, and reinfuse the filtered blood into the vasculature.

14. The system of claim 11, wherein: the impermeable membrane is a continuous membrane extending from a base of the reinforcement structure to a distal most end of the reinforcement structure; and an inner surface of the expandable funnel shaped distal end is configured to enhance a laminar flow circumferentially along the inner surface to generate a vortex effect during the suction force.

15. The system of claim 14, further comprising a fragmentor configured to fragment undesirable material entrapped within the expandable funnel shaped distal end and thereby enhance the suction force to aspirate the undesirable material substantially en bloc.

16. The system of claim 11, wherein: the cannula is comprised of a pliable material and a reinforcement wire; and the cannula is configured to optimize maneuverability within the vasculature without kinking.

17. The system of claim 11, wherein a combination of the first filter membrane and the second filter membrane is configured to result in an enhanced filtration such that substantially all of the undesirable material is filtered from the aspirated blood, thereby reducing the probability of substantially any of the undesirable material from exiting the outlet.

18. A system comprising:

a cannula comprising a funnel shaped distal end and a lumen, the funnel shaped distal end comprising an expandable reinforcement structure and an impermeable membrane, the impermeable membrane being coupled to the expandable reinforcement structure;

a pump configured to be operably coupled to the cannula, wherein the pump is configured to create a suction force sufficient to aspirate undesirable material and blood from a vasculature towards the cannula lumen;

an agitator configured to engage with the undesirable material when positioned within the funnel shaped distal end; and a filter assembly configured to receive the aspirated undesirable material and blood, the filter assembly comprising an inlet, an outlet, a first filter membrane, a second filter membrane, and a fluid path extending from the inlet through the first and second filter membranes and to the outlet, wherein the first and second filter membranes are configured to permit the aspirated blood to flow along the fluid path from the inlet to the outlet and inhibit the undesirable material from flowing along the fluid path from the inlet to the outlet, wherein the second filter membrane is positioned downstream from the first filter membrane, and the first filter membrane comprises a first filter pore size and the second filter membrane comprises a second filter pore size, the first filter pore size being larger than the second filter pore size, and wherein the filter assembly further comprises a venting aperture for displacing air from the filter assembly.

19. The system of claim 18, wherein the funnel shaped distal end and the agitator together are configured to generate a vortex effect when the suction force is applied by the pump.

20. The system of claim 18, further comprising:

a first container configured to receive the aspirated undesirable material from the cannula and operably couple to the filter assembly;

a second container configured to operably couple to the filter assembly and receive the filtered blood; and a reinfusion cannula configured to operably couple to the second container, and the reinfusion cannula being configured to be placed in the vasculature, and flow the filtered blood into the vasculature.

21. The system of claim 18, wherein the agitator includes a rheolytic or fragmentation device.

22. A system comprising:

a blood collection and filtration assembly;

a cannula comprising a funnel shaped distal end and a lumen, the funnel shaped distal end comprising an expandable reinforcement structure and an impermeable membrane, the cannula being configured to be operably coupled to the blood collection and filtration assembly;

a vacuum source configured to create a negative pressure through the cannula lumen and the blood collection and filtration assembly sufficient to aspirate undesirable material and blood from a vasculature;

wherein the blood collection and filtration assembly comprises an inlet, a first filter assembly, a second filter assembly, a reservoir, an outlet, and a fluid path extending from the inlet, through the first filter assembly, the second filter assembly, the reservoir, and to the outlet; and wherein the blood collection and filtration assembly is configured to receive the aspirated undesirable material and aspirated blood from the cannula through the inlet, and both the first filter assembly and the second filter assembly are configured to permit the aspirated blood to flow along the fluid path from the inlet to the outlet and inhibit the undesirable material from flowing along the fluid path from the inlet to the outlet, thereby filtering the aspirated undesirable material from the aspirated blood to produce filtered blood, the reservoir is configured to capture the undesirable material, and wherein the second filter assembly is positioned downstream from the first filter assembly, and the first filter assembly comprises a first filter pore size and the second filter assembly comprises a second filter pore size, the first filter pore size being larger than the second filter pore size, and wherein a combination of the first filter assembly and the second filter assembly is configured to result in an enhanced filtration such that substantially all of the undesirable material is filtered from the aspirated blood, thereby reducing the probability of substantially any of the undesirable material from exiting the outlet.

23. The system of claim 22, further comprising an agitator to aid in removal of the undesirable material from the vasculature, where the agitator is configured to engage with the undesirable material within the funnel shaped distal end.

24. The system of claim 22, wherein the blood collection and filtration assembly further comprises a venting aperture configured to vent air from the blood collection assembly, the venting aperture is configured to be above a fluid level of the reservoir.

25. The system of claim 24, wherein the reservoir is configured to visualize the captured undesirable material.

26. The system of claim 22, wherein the funnel shaped distal end is configured to generate a vortex flow.

27. The system of claim 22, further comprising a reinfusion assembly configured to receive the filtered blood, wherein the reinfusion assembly comprises a reinfusion cannula configured to be placed in the vasculature and reinfuse the filtered blood into the vasculature.

28. The system of claim 22, wherein the vacuum source is configured to be in operative fluid communication with the blood collection and filtration assembly and the cannula.

29. The system of claim 22, wherein the blood collection and filtration assembly further comprises a first conduit coupled to the inlet and a second conduit coupled to the outlet, wherein the first conduit is configured to be operably coupled to the cannula and the second conduit is configured to be operably coupled to the vacuum source.

30. The system of claim 22, wherein the blood collection and filtration assembly is positioned between the cannula and the vacuum source.

* * * * *